United States Patent [19]
Williams et al.

[11] Patent Number: 5,744,313
[45] Date of Patent: Apr. 28, 1998

[54] ASSAY EMPLOYING NOVEL PROTEIN DOMAIN WHICH BINDS TYROSINE PHOSPHORYLATED PROTEINS

[75] Inventors: Lewis T. Williams, Tiburon; William Michael Kavanaugh, Mill Valley, both of Calif.

[73] Assignee: The Regents of the University of California, Oakland, Calif.

[21] Appl. No.: 353,550

[22] Filed: Dec. 9, 1994

[51] Int. Cl.$^6$ ................................................. G01N 33/53
[52] U.S. Cl. ........................... 435/7.1; 435/7.2; 435/6; 436/501
[58] Field of Search .................... 435/6, 7.1, 7.2, 435/501

[56] References Cited

U.S. PATENT DOCUMENTS 5,352,660  10/1994  Pawson ................................... 514/12

FOREIGN PATENT DOCUMENTS

WO 92/13001  8/1992  WIPO.

OTHER PUBLICATIONS

Damen et al, *Blood* 82(8):2296–3303, 15 Oct. 1993.
Adams, "3,400 new expressed sequence tags identify diversity of transcripts in human brain," *Nature Genetics* 4:256–267 (1993).
Bibbins et al., "Binding of the Src SH2 domain phosphopeptides is determined by residues in both the SH2 domain and the phosphopeptides," *Mol. Cell. Biol.* 13:7278–7287 (1993).
Birge et al., "Tyrosine-phosphorylated epidermal growth factor receptor and cellular p130 provide high affinity binding substrates to analyze Crk-phosphotyrosine-dependent interactions in vitro," *J. Biol. Chem.* 267:10588–10595 (1992).
Cantley et al., "Oncogenes and signal transduction," *Cell* 64:281–302 (1991).
Egan et al., "Association of Sos Ras exchange protein with Grb2 is implicated in tyrosine kinase signal transduction and transformation," *Nature* 363:45–51 (1993).
Escobedo et al., "A phosphatidylinositol-3 kinase binds to platelet-derived growth factor receptors through a specific receptor sequence containing phosphotyrosine," *Mol. Cell. Biol.* 11:1125–1132 (1991).
Katzav "Single point mutations in the SH2 domain impair the transforming potential of vav and fail to activate proto-vav," *Oncogene* 8:1757–1763 (1993).

Kavanaugh et al., "Modification of the 85-kilodalton subunit of phosphatidylinosiol-3 kinase in platelet-derived growth factor-stimulated cells," *Mol. Cell. Biol.* 12:3415–3424 (1992).
Marengere et al., "Identification of residues in GTPase-activating protein Src homology 2 domains that control binding to tyrosine phosphorylated growth factor receptors and p62," *J. Biol. Chem.* 267:22779–22786 (1992).
Mayer et al., "Point mutations in the abl SH2 domain coordinately impair phosphotyrosine binding in vitro and transforming activity in vivo," *Mol. Cell. Biol.* 12:609–618 (1992).
Pawson et al., "SH2 and SH3 domains: From structure to function," *Cell* 71:359–362 (1992).
Pelicci et al., "A novel transforming protein (SHC) with an SH2 domain is implicated in mitogenic signal transduction," *Cell* 70:93–104 (1992).
Rozakis-Adcock et al., "Association of the Shc and Grb2/Sem5 SH2-containing proteins is implicated in activation of the Ras pathway by tyrosine kinases," *Nature* 360:689–692 (1992).
Sadowski et al., "A noncatalytic domain conserved among cytoplasmic protein-tyrosine kinases modifies the kinase function and transforming activity of Fujinami sarcoma virus P130gag-fps," *Mol. Cell. Biol.* 6:4396–4408 (1986).
Songyang et al., "SH2 domains recognize specific phosphopeptide sequences," *Cell* 72:767–778 (1993).
Waksman et al., "Binding of a high affinity phosphotyrosyl peptide to the Src SH2 domain: crystal structures of the complexed and peptide-free forms," *Cell* 72:779–790 (1993).

*Primary Examiner*—John Ulm
*Attorney, Agent, or Firm*—Townsend & Townsend & Crew LLP

[57] ABSTRACT

The present invention generally relates to novel protein domains which bind to tyrosine-phosphorylated proteins. More particularly, the present invention provides non-SH2 protein domains that bind phosphotyrosine. The present invention also provides various composite polypeptides comprising these domains, such that these composite polypeptides retain the ability to bind tyrosine phosphorylated proteins. It also provides nucleic acids encoding these polypeptides. Typically, these nucleic acids may also comprise a promoter for expression, and a segment encoding fusion peptides on the amino or carboxy terminus of the expressed composite protein. Also included within the present invention are methods of preparing these polypeptides and cells capable of expressing them. Also provided are methods of using these polypeptides in research, diagnostic and therapeutic applications.

21 Claims, 12 Drawing Sheets

```
                                                            * * * *
SCK  ..pgsGdaaa  aaEWiRkGSF  ihKPahGWLH  PdarV lGPGV  SYvVRYMGCi
SHC  rtrveGgqig  geEWtRhGSF  vnKPtrGWLH  PndkV mGPGV  SYlVRYMGCv SCK  EVLrSMRsLD  FNTRTQVTRE  AInrihEAVP  GvrGs.wkkK  apnkaLaSvL
SHC  EVLqSMRaLD  FNTRTQVTRE  AIslvcEAVP  GakGatrrrK  pcsrpLsSiL SCK  GkSNLrFAGM  sIsihiSTdg  LsLsvpatrQ  vLANHHMpSI  SFASGGDtDm
SHC  GrSNLkFAGM  pItltvSTss  LnLmaadckQ  iLANHHMqSI  SFASGGDpDt SCK  tdYVAYVAKD  PiNQRACHIL  ECcEGLAQsi  ISTvGQAFEL  RFKQYLhsPP
SHC  aeYVAYVAKD  PiNQRACHIL  ECpEGLAQdv  ISTiGQAFEL  RFKQYLrnPP SCK  KvalPpeRlA  GpeeSAWg.d  EEdslEHnYY  NsiPGKEPPL  GGlVDsRLal
SHC  KlvtPhdRmA  GfdgSAWdEe  EEeppDHqYY  NdfPGKEPPL  GGvVDmRL..

SCK  tqpcAltald  qgpsPslrda  csLpwdvgst  GtappGDgyV  qadargPPd.
SHC  .regAapgaa  rptaPnaqtp  shLgatl.pv  GqpvgDpeV   rkqmppPPpc SCK  .....heehl  YVNtQgLD..  ..........  APepedSpkk  DLFDMrPFED
SHC  pgrelfddps  YVNvQnLDka  rqavggagpp  NPaingSapr  DLFDMkPFED SCK  ALklhecsva  agvtaaplpl  edqwpsPPtr  rapvApteEQ  LRqEPWyHGr
SHC  ALrv......  ..........  .....pPPpq  svsmA...EQ  LRgEPWfHGk SCK  mSRRaAErmL  radGDFLVRd  SvTnPGQYVL  TGmhaGQPKH  LLLVDPEGVV
SHC  lSRReAEalL  qlnGDFLVRe  StTtPGQYVL  TGlqsGQPKH  LLLVDPEGVV
```

*FIG. 4.*

```
         10        20        30        40        50
CCGGGGTCCGGGGACGCCGCCGCCGCCGAGTGGATCCGGAAGGGCAGCTTCATCC
GGCCCCAGGCCCCTGCGGCGGCGGCGGCGGCTCACCTAGGCCTTCCCGTCGAAGTAGG
  P  G  S  G  D  A  A  A  A  A  E  W  I  R  K  G  S  F  I 60        70        80        90       100       110
ACAAACCCGCGCACGGCTGGCTACACCCCGACGCCAGGGTCCTGGGGCCCGGGGTCTC
TGTTTGGGCGCGTGCCGACCGATGTGGGGCTGCGGTCCCAGGACCCCGGGCCCCAGAG
  H  K  P  A  H  G  W  L  H  P  D  A  R  V  L  G  P  G  V  S 120       130       140       150       160       170
CTACGTCGTGCGGTACATGGGCTGCATCGAGGTTCTCCGCTCTATGCGCTCCCTGGAC
GATGCAGCACGCCATGTACCCGACGTAGCTCCAAGAGGCGAGATACGCGAGGGACCTG
  Y  V  V  R  Y  M  G  C  I  E  V  L  R  S  M  R  S  L  D 180       190       200       210       220       230
TTTAACACGCGCACGCAGGTGACCAGGGAAGCCATCAACCGGCTCCATGAGGCCGTGC
AAATTGTGCGCGTGCGTCCACTGGTCCCTTCGGTAGTTGGCCGAGGTACTCCGGCACG
  F  N  T  R  T  Q  V  T  R  E  A  I  N  R  L  H  E  A  V 240       250       260       270       280       290
CTGGCGTCCGGGGATCCTGGAAGAAAAAGGCCCCCAACAAGGCCCTGGCGTCCGTCCT
GACCGCAGGCCCCTAGGACCTTCTTTTTCCGGGGGTTGTTCCGGGACCGCAGGCAGGA
  P  G  V  R  G  S  W  K  K  K  A  P  N  K  A  L  A  S  V  L 300       310       320       330       340
GGGCAAGAGCAACCTTCGCTTTGCCGGCATGAGCATCTCCATCCACATCTCCACTGAT
CCCGTTCTCGTTGGAAGCGAAACGGCCGTACTCGTAGAGGTAGGTGTAGAGGTGACTA
  G  K  S  N  L  R  F  A  G  M  S  I  S  I  H  I  S  T  D 360       370       380       390       400
GGCCTCAGCCTCTCCGTGCCTGCCACGCGCCAGGTCATCGCCAACCACCACATGCCGT
CCGGAGTCGGAGAGGCACGGACGGTGCGCGGTCCAGTAGCGGTTGGTGGTGTACGGCA
  G  L  S  L  S  V  P  A  T  R  Q  V  I  A  N  H  H  M  P 410       420       430       440       450       460
CCATCTCCTTCGCGTCAGGCGGAGACACGGACATGACGGATTACGTGGCCTACGTCGC
GGTAGAGGAAGCGCAGTCCGCCTCTGTGCCTGTACTGCCTAATGCACCGGATGCAGCG
  S  I  S  F  A  S  G  D  T  D  M  T  D  Y  V  A  Y  V  A 470       480       490       500       510       520
CAAGGACCCCATCAACCAGAGAGCCTGCCACATCCTGGAGTGCTGTGAGGGCCTGGCA
GTTCCTGGGGTAGTTGGTCTCTCGGACGGTGTAGGACCTCACGACACTCCCGGACCGT
  K  D  P  I  N  Q  R  A  C  H  I  L  E  C  C  E  G  L  A
```

FIG. 5A.

```
      530        540        550        560        570        580
CAGAGCATCATCAGCACCGTGGGCCAAGCTTTCGAGCTGCGCTTCAAGCAGTACCTGC
GTCTCGTAGTAGTCGTGGCACCCGGTTCGAAAGCTCGACGCGAAGTTCGTCATGGACG
 Q   S   I   I   S   T   V   G   Q   A   F   E   L   R   F   K   Q   Y   L 590        600        610        620        630
ACAGCCCGCCCAAGGTGGCGCTGCCCCCAGAAAGGCTGGCAGGGCCGGAGGAGTCGGC
TGTCGGGCGGGTTCCACCGCGACGGGGGTCTTTCCGACCGTCCCGGCCTCCTCAGCCG
 H   S   P   P   K   V   A   L   P   P   E   R   L   A   G   P   E   E   S   A 650        660        670        680        690
CTGGGGGGACGAGGAGGACTCTTTGGAGCACAATTACTACAACAGCATCCCGGGGAAG
GACCCCCCTGCTCCTCCTGAGAAACCTCGTGTTAATGATGTTGTCGTAGGGCCCCTTC
 W   G   D   E   E   D   S   L   E   H   N   Y   Y   N   S   I   P   G   K 700        710        720        730        740        750
GAGCCGCCGCTGGGCGGGCTAGTGGACTCCAGGCTGGCCCTGACACAGCCCTGCGCCC
CTCGGCGGCGACCCGCCCGATCACCTGAGGTCCGACCGGGACTGTGTCGGGACGCGGG
 E   P   P   L   G   G   L   V   D   S   R   L   A   L   T   Q   P   C   A 760        770        780        790        800        810
TCACGGCCCTCGACCAGGGCCCATCTCCTTCTCTAAGAGATGCCTGCAGCCTGCCATG
AGTGCCGGGAGCTGGTCCCGGGTAGAGGAAGAGATTCTCTACGGACGTCGGACGGTAC
 L   T   A   L   D   Q   G   P   S   P   S   L   R   D   A   C   S   L   P   W 820        830        840        850        860        870
GGACGTGGGGTCCACCGGTACAGCTCCACCGGGGGACGGCTACGTGCAGGCGGACGCC
CCTGCACCCCAGGTGGCCATGTCGAGGTGGCCCCCTGCCGATGCACGTCCGCCTGCGG
 D   V   G   S   T   G   T   A   P   P   G   D   G   Y   V   Q   A   D   A 880        890        900        910        920
CGGGGCCCCCCGGACCACGAGGAGCACCTGTATGTCAACACCCAGGGTCTGGACGCCC
GCCCCGGGGGGCCTGGTGCTCCTCGTGGACATACAGTTGTGGGTCCCAGACCTGCGGG
 R   G   P   P   D   H   E   E   H   L   Y   V   N   T   Q   G   L   D   A 940        950        960        970        980
CCGAGCCGGAGGACAGCCCCAAAAAGGATCTGTTTGACATGCGACCCTTTGAGGATGC
GGCTCGGCCTCCTGTCGGGGTTTTTCCTAGACAAACTGTACGCTGGGAAACTCCTACG
 P   E   P   E   D   S   P   K   K   D   L   F   D   M   R   P   F   E   D   A 990       1000       1010       1020       1030       1040
CCTGAAGTTGCATGAGTGCTCAGTGGCGGCAGGCGTGACAGCAGCCCCTCTTCCCTTG
GGACTTCAACGTACTCACGAGTCACCGCCGTCCGCACTGTCGTCGGGGAGAAGGGAAC
 L   K   L   H   E   C   S   V   A   A   G   V   T   A   A   P   L   P   L
```

FIG. 5B.

```
      1050       1060       1070       1080       1090       1100
GAGGACCAGTGGCCCAGCCCCCCTACCCGCCGGGCCCCTGTGGCCCCCACGGAGGAAC
CTCCTGGTCACCGGGTCGGGGGGATGGGCGGCCCGGGGACACCGGGGGTGCCTCCTTG
  E   D   Q   W   P   S   P   P   T   R   R   A   P   V   A   P   T   E   E 1110       1120       1130       1140       1150       1160
AGCTGCGTCAGGAGCCCTGGTACCACGGCCGGATGAGCCGCCGGGCGGCAGAGAGGAT
TCGACGCAGTCCTCGGGACCATGGTGCCGGCCTACTCGGCGGCCCGCCGTCTCTCCTA
  Q   L   R   Q   E   P   W   Y   H   G   R   M   S   R   R   A   A   E   R   M 1170       1180       1190       1200       1210
GCTTCGAGCTGACGGGGACTTCCTTGTGCGAGACAGCGTCACCAACCCCGGGCAGTAT
CGAAGCTCGACTGCCCCTGAAGGAACACGCTCTGTCGCAGTGGTTGGGGCCCGTCATA
  L   R   A   D   G   D   F   L   V   R   D   S   V   T   N   P   G   Q   Y 1230       1240       1250       1260       1270
GTCCTCACCGGCATGCACGCCGGGCAGCCCAAGCACCTGCTGCTCGTGGACCCCGAGG
CAGGAGTGGCCGTACGTGCGGCCCGTCGGGTTCGTGGACGACGAGCACCTGGGGCTCC
  V   L   T   G   M   H   A   G   Q   P   K   H   L   L   L   V   D   P   E 1280       1290       1300       1310       1320       1330
GCGTGGTACGGACGAAGGACGTGCTGTTTGAGAGCATCAGCCACCTGATCGACCACCA
CGCACCATGCCTGCTTCCTGCACGACAAACTCTCGTAGTCGGTGGACTAGCTGGTGGT
  G   V   V   R   T   K   D   V   L   F   E   S   I   S   H   L   I   D   H   H 1340       1350       1360       1370       1380       1390
CCTGCAGAACGGGCAGCCCATCGTGGCCGCCGAGAGTGAGCTGCACCTGCGTGGCGTG
GGACGTCTTGCCCGTCGGGTAGCACCGGCGGCTCTCACTCGACGTGGACGCACCGCAC
  L   Q   N   G   Q   P   I   V   A   A   E   S   E   L   H   L   R   G   V 1400       1410
GTCTCACGGGAGCCCTGA
CAGAGTGCCCTCGGGACT
  V   S   R   E   P
```

*FIG. 5C.*

```
           10        20        30        40        50
ATGAACAAGCTGAGTGGAGGCGGCGGGCGCAGGACTCGGGTGGAAGGGGGCCAGCTTG
TACTTGTTCGACTCACCTCCGCCGCCCGCGTCCTGAGCCCACCTTCCCCCGGTCGAAC
 M  N  K  L  S  G  G  G  R  R  T  R  V  E  G  G  Q  L 60        70        80        90       100       110
GGGGCGAGGAGTGGACCCGCCACGGGAGCTTTGTCAATAAGCCCACGCGGGGCTGGCT
CCCCGCTCCTCACCTGGGCGGTGCCCTCGAAACAGTTATTCGGGTGCGCCCCGACCGA
 G  G  E  E  W  T  R  H  G  S  F  V  N  K  P  T  R  G  W  L 120       130       140       150       160       170
GCATCCCAACGACAAAGTCATGGGACCCGGGGTTTCCTACTTGGTTCGGTACATGGGT
CGTAGGGTTGCTGTTTCAGTACCCTGGGCCCCAAAGGATGAACCAAGCCATGTACCCA
 H  P  N  D  K  V  M  G  P  G  V  S  Y  L  V  R  Y  M  G 180       190       200       210       220       230
TGTGTGGAGGTCCTCCAGTCAATGCGTGCCCTGGACTTCAACACCCGGACTCAGGTCA
ACACACCTCCAGGAGGTCAGTTACGCACGGGACCTGAAGTTGTGGGCCTGAGTCCAGT
 C  V  E  V  L  Q  S  M  R  A  L  D  F  N  T  R  T  Q  V 240       250       260       270       280       290
CCAGGGAGGCCATCAGTCTGGTGTGTGAGGCTGTGCCGGGTGCTAAGGGGGCGACAAG
GGTCCCTCCGGTAGTCAGACCACACACTCCGACACGGCCCACGATTCCCCCGCTGTTC
 T  R  E  A  I  S  L  V  C  E  A  V  P  G  A  K  G  A  T  R 300       310       320       330       340
GAGGAGAAAGCCCTGTAGCCGCCCGCTCAGCTCTATCCTGGGGAGGAGTAACCTGAAA
CTCCTCTTTCGGGACATCGGCGGGCGAGTCGAGATAGGACCCCTCCTCATTGGACTTT
 R  R  K  P  C  S  R  P  L  S  S  I  L  G  R  S  N  L  K 360       370       380       390       400
TTTGCTGGAATGCCAATCACTCTCACCGTCTCCACCAGCAGCCTCAACCTCATGGCCG
AAACGACCTTACGGTTAGTGAGAGTGGCAGAGGTGGTCGTCGGAGTTGGAGTACCGGC
 F  A  G  M  P  I  T  L  T  V  S  T  S  S  L  N  L  M  A 410       420       430       440       450       460
CAGACTGCAAACAGATCATCGCCAACCACCACATGCAATCTATCTCATTTGCATCCGG
GTCTGACGTTTGTCTAGTAGCGGTTGGTGGTGTACGTTAGATAGAGTAAACGTAGGCC
 A  D  C  K  Q  I  I  A  N  H  H  M  Q  S  I  S  F  A  S  G 470       480       490       500       510       520
CGGGGATCCGGACACAGCCGAGTATGTCGCCTATGTTGCCAAAGACCCTGTGAATCAG
GCCCCTAGGCCTGTGTCGGCTCATACAGCGGATACAACGGTTTCTGGGACACTTAGTC
 G  D  P  D  T  A  E  Y  V  A  Y  V  A  K  D  P  V  N  Q
```

*FIG. 6A.*

```
      530       540       550       560       570       580
AGAGCCTGCCACATTCTGGAGTGTCCCGAAGGGCTTGCCCAGGATGTCATCAGCACCA
TCTCGGACGGTGTAAGACCTCACAGGGCTTCCCGAACGGGTCCTACAGTAGTCGTGGT
  R   A   C   H   I   L   E   C   P   E   G   L   A   Q   D   V   I   S   T 590       600       610       620       630
TTGGCCAGGCCTTCGAGTTGCGCTTCAAACAATACCTCAGGAACCCACCCAAACTGGT
AACCGGTCCGGAAGCTCAACGCGAAGTTTGTTATGGAGTCCTTGGGTGGGTTTGACCA
  I   G   Q   A   F   E   L   R   F   K   Q   Y   L   R   N   P   P   K   L   V 650       660       670       680       690
CACCCCTCATGACAGGATGGCTGGCTTTGATGGCTCAGCATGGGATGAGGAGGAGGAA
GTGGGGAGTACTGTCCTACCGACCGAAACTACCGAGTCGTACCCTACTCCTCCTCCTT
  T   P   H   D   R   M   A   G   F   D   G   S   A   W   D   E   E   E   E 700       710       720       730       740       750
GAGCCACCTGACCATCAGTACTATAATGACTTCCCGGGGAAGGAACCCCCCTTGGGGG
CTCGGTGGACTGGTAGTCATGATATTACTGAAGGGCCCCTTCCTTGGGGGGAACCCCC
  E   P   P   D   H   Q   Y   Y   N   D   F   P   G   K   E   P   P   L   G 760       770       780       790       800       810
GGGTGGTAGACATGAGGCTTCGGGAAGGAGCCGCTCCAGGGGCTGCTCGACCCACTGC
CCCACCATCTGTACTCCGAAGCCCTTCCTCGGCGAGGTCCCCGACGAGCTGGGTGACG
  G   V   V   D   M   R   L   R   E   G   A   A   P   G   A   A   R   P   T   A 820       830       840       850       860       870
ACCCAATGCCCAGACCCCCAGCCACTTGGGAGCTACATTGCCTGTAGGACAGCCTGTT
TGGGTTACGGGTCTGGGGGTCGGTGAACCCTCGATGTAACGGACATCCTGTCGGACAA
  P   N   A   Q   T   P   S   H   L   G   A   T   L   P   V   G   Q   P   V 880       890       900       910       920
GGGGGAGATCCAGAAGTCCGCAAACAGATACCACCTCCACCACCCTGTCCAGCAGGCA
CCCCCTCTAGGTCTTCAGGCGTTTGTCTATGGTGGAGGTGGTGGGACAGGTCGTCCGT
  G   G   D   P   E   V   R   K   Q   M   P   P   P   P   P   C   P   A   G 940       950       960       970       980
GAGAGCTTTTTGATGATCCCTCCTATGTCAACGTCCAGAACCTAGACAAGGCCCGGCA
CTCTCGAAAAACTACTAGGGAGGATACAGTTGCAGGTCTTGGATCTGTTCCGGGCCGT
  R   E   L   F   D   D   P   S   Y   V   N   V   Q   N   L   D   K   A   R   Q 990       1000      1010      1020      1030      1040
AGCAGTGGGTGGTGCTGGGCCCCCAATCCTGCTATCAATGGCAGTGCACCCCGGGAC
TCGTCACCCACCACGACCCGGGGGGTTAGGACGATAGTTACCGTCACGTGGGGCCCTG
  A   V   G   G   A   G   P   P   N   P   A   I   N   G   S   A   P   R   D
```

FIG. 6B.

```
          1050        1060        1070        1080        1090        1100
CTGTTTGACATGAAGCCCTTCGAAGATGCTCTTCGGGTGCCTCCACCTCCCCAGTCGG
GACAAACTGTACTTCGGGAAGCTTCTACGAGAAGCCCACGGAGGTGGAGGGGTCAGCC
  L   F   D   M   K   P   F   E   D   A   L   R   V   P   P   P   Q   S 1110        1120        1130        1140        1150        1160
TGTCCATGGCTGAGCAGCTCCGAGGGGAGCCCTGGTTCCATGGGAAGCTGAGCCGGCG
ACAGGTACCGACTCGTCGAGGCTCCCCTCGGGACCAAGGTACCCTTCGACTCGGCCGC
  V   S   M   A   E   Q   L   R   G   E   P   W   F   H   G   K   L   S   R   R 1170        1180        1190        1200        1210
GGAGGCTGAGGCACTGCTGCAGCTCAATGGGGACTTCCTGGTACGGGAGAGCACGACC
CCTCCGACTCCGTGACGACGTCGAGTTACCCCTGAAGGACCATGCCCTCTCGTGCTGG
  E   A   E   A   L   L   Q   L   N   G   D   F   L   V   R   E   S   T   T 1230        1240        1250        1260        1270
ACACCTGGCCAGTATGTGCTCACTGGCTTGCAGAGTGGGCAGCCTAAGCATTTGCTAC
TGTGGACCGGTCATACACGAGTGACCGAACGTCTCACCCGTCGGATTCGTAAACGATG
  T   P   G   Q   Y   V   L   T   G   L   Q   S   G   Q   P   K   H   L   L 1280        1290        1300        1310        1320        1330
TGGTGGACCCTGAGGGTGTGGTTCGGACTAAGGATCACCGCTTTGAAAGTGTCAGTCA
ACCACCTGGGACTCCCACACCAAGCCTGATTCCTAGTGGCGAAACTTTCACAGTCAGT
  L   V   D   P   E   G   V   V   R   T   K   D   H   R   F   E   S   V   S   H 1340        1350        1360        1370        1380        1390
CCTTATCAGCTACCACATGGACAATCACTTGCCCATCATCTCTGCGGGCAGCGAACTG
GGAATAGTCGATGGTGTACCTGTTAGTGAACGGGTAGTAGAGACGCCCGTCGCTTGAC
  L   I   S   Y   H   M   D   N   H   L   P   I   I   S   A   G   S   E   L 1400        1410        1420
TGTCTACAGCAACCTGTGGAGCGGAAACTGTGA
ACAGATGTCGTTGGACACCTCGCCTTTGACACT
  C   L   Q   Q   P   V   E   R   K   L
```

*FIG. 6C.*

ASSAY EMPLOYING NOVEL PROTEIN DOMAIN WHICH BINDS TYROSINE PHOSPHORYLATED PROTEINS

The present invention was made with U.S. Government support under Grant Nos. R01 HL32898 and K11 HL02714, awarded by the National Institutes of Health. The government has certain rights in this invention.

The present invention generally relates to novel protein domains that specifically bind to tyrosine-phosphorylated proteins. More particularly, the present invention provides non-SH2 protein domains that bind phosphotyrosine. The present invention also provides various composite polypeptides comprising these domains, such that these composite polypeptides retain the ability to bind tyrosine phosphorylated proteins. It also provides nucleic acids encoding these polypeptides. Typically, these nucleic acids can also comprise a promoter for expression, and a segment encoding fusion peptides on the amino or carboxy terminus of the expressed composite protein. Also included within the present invention are methods of preparing these polypeptides and cells capable of expressing them. Also provided are methods of using these polypeptides in diagnostic and therapeutic applications.

BACKGROUND OF THE INVENTION

Receptor signaling pathways are the subject of widespread research efforts. A better understanding of these signaling pathways will lead to the design of new and more effective drugs in the treatment of many diseases. Of particular interest are the growth factor and related receptor signaling pathways and their role in cell growth and differentiation. Binding of a particular growth factor to its receptor on the cell plasma membrane can stimulate a wide variety of biochemical responses, including changes in ion fluxes, activation of various kinases, alteration of cell shape, transcription of various genes and modulation of enzymatic activities in cellular metabolism.

In particular, upon binding an external ligand, a receptor may undergo auto-phosphorylation of specific tyrosine residues, and/or may phosphorylate other proteins. This tyrosine phosphorylation creates binding sites for cytoplasmic signaling proteins which have specific domains that recognize the phosphorylated tyrosine and adjacent residues. Once bound, these signaling proteins may in turn be activated. The activated signaling proteins then may effect downstream processes. Pawson and Gish, *Cell* 71:359–362 (1992).

SH2 (which stands for Src Homologous) domains are amino acid sequences that are similar to a 100-residue, non-catalytic region of the Src tyrosine kinase and are present in various signaling molecules. Sadowski et al., *Mol. Cell. Biol.* 6, 4396 (1986). SH2 domains are the functional protein motifs that bind tyrosine-phosphorylated targets by recognizing phosphotyrosine and specific adjacent residues. J. A. Escobedo et al., *Mol. Cell. Biol.* 11, 1125 (1991); L. C. Cantley et al. *Cell* 64, 281 (1991); T. Pawson and G. D. Gish *Cell* 71, 359 (1992); S. Zhou et al. *Cell* 72, 767 (1993); G. Waksman, S. E. Shoelson, N. Pant, D. Cowburn, J. Kuriyan *Cell* 72, 779 (1993). Activation of tyrosine kinases by growth factors, cytokines, and oncogenic agents therefore serves as a switch for assembling SH2 domain-containing proteins with their tyrosine-phosphorylated targets in signaling complexes, in which downstream effectors are activated.

The use of tyrosine kinase binding domains, including SH2 domains, has been discussed in methods for identifying targets of tyrosine kinases in cells, and thus identifying intermediates in cell signaling pathways. See, PCT Patent Application No. WO 92/13001, to Schlessinger et al.

The specific use of SH2 domains and subdomains in affecting the SH2 phosphorylated ligand regulatory scheme, or screening for compounds which affect SH2 binding in the SH2 phosphorylated regulatory scheme, as well as in assaying for the presence of SH2 binding phosphoproteins, has generally been described. See, U.S. Pat. No. 5,352,660 to A. J. Pawson.

Specific SH2 containing proteins include the products of the SHC gene. The SHC (which stands for SH2, Collagen) gene encodes a transforming protein expressed as 46- and 52-kD proteins, that are tyrosine phosphorylated in response to a number of growth factors, e.g., PDGF, EGF and FGF, and have been implicated as mediators of signaling from growth factor receptor and non-receptor tyrosine kinases to Ras. G. Pelicci et al. *Cell* 70, 93–104 (1992); M. Rozakis-Adcock et al. *Nature*, 360:689 (1992).

Thus, a great deal of attention has been directed toward studying these SH2 domains and their role in cell signaling pathways. However, SH2 domains, and the proteins which comprise them, are not the only phosphotyrosine binding mediators of such pathways. Accordingly, the study of these pathways, and the ability to control them requires identification and characterization of other phosphotyrosine binding domains. The present invention meets these and other needs.

SUMMARY OF THE INVENTION

One aspect of the present invention provides an isolated polypeptide comprising a non-SH2 phosphotyrosine binding ("PTB") domain. Such polypeptides are capable of binding a tyrosine-phosphorylated protein through the non-SH2 PTB domain. Preferably, the isolated polypeptide comprises an amino acid sequence that is substantially homologous to the amino acid sequence of the SHC protein PTB domain, and more preferably the polypeptide comprises the amino acid sequence of either the SHC PTB domain or a SHC-like ("SCK") PTB domain. The polypeptide can be in the form of a fusion protein, or can comprise a detectable group attached thereto.

In an alternative embodiment is provided an isolated nucleic acid comprising a segment which encodes a non-SH2 PTB domain. Preferably, the nucleic acid comprises a nucleotide sequence that is substantially homologous to the nucleotide sequence which encodes the SHC PTB domain, and more preferably, comprises the nucleotide sequence encoding the SHC PTB domain or SCK PTB domain. The nucleic acid sequence may further comprise a segment which encodes a heterologous protein fused to the PTB domain encoding segment. Also provided are expression vectors comprising the above nucleic acids operably linked to a promoter sequence.

Also provided are methods of preparing the polypeptides of the present invention. The methods comprise inserting the nucleic acids of the present invention in a suitable expression vector, transfecting a host cell with the expression vector, such that the cell is capable of expressing the non-SH2 PTB domain, and recovering the non-SH2 PTB domain.

Further provided are nucleic acid probes, comprising at least 15 consecutive nucleotides of the nucleotide sequence which encodes the SHC or SCK PTB domains, and wherein the probes are linked to a detectable group.

Also provided is a method of determining whether a protein is a phosphorylated ligand of a PTB domain. The method comprises contacting the protein with a polypeptide of the present invention and detecting the binding of the polypeptide to the protein. The binding of the polypeptide to the protein is indicative that the protein is a phosphorylated ligand of the PTB domain.

In a related aspect, the present invention provides a method of determining whether a test compound is an antagonist of a growth factor activation signaling pathway in a cell. The method comprises contacting the cell with the test compound in the presence of a growth factor. The cells are then lysed and the cell lysate is assayed to determine whether any protein in the lysate is a phosphorylated ligand to a PTB domain. The absence of the phosphorylated ligand is indicative that the compound is an antagonist of the growth factor activation signaling pathway.

In another related aspect, the invention provides a method of determining if a test compound is an agonist or antagonist of a PTB domain/phosphorylated ligand regulatory system. The method comprises incubating the test compound with a polypeptide comprising a PTB domain, and a phosphorylated ligand which is capable of interacting with said PTB domain to form a PTB domain/phosphorylated ligand complex, under conditions which permit the formation of said complex. The amount of PTB domain/phosphorylated ligand complex formed is determined, and compared to the amount of PTB domain/phosphorylated ligand complex formed in the absence of the test compound. The increase or decrease in the amount of complex formed in the presence of the test compound over the amount of complex formed in the absence of the test compound is indicative that the test compound is an agonist or antagonist of the PTB domain/ phosphorylated ligand regulatory system.

In a further aspect is provided a method of blocking growth factor dependent stimulation of cells, comprising contacting the cells with an effective amount of the polypeptides of the present invention.

In an additional embodiment is provided method of obtaining substantially pure phosphorylated ligand to a PTB domain from a mixture of different proteins comprising contacting the mixture of different proteins with a PTB domain immobilized on a solid support, whereby the phosphorylated ligand is bound to the PTB domain. The solid support is washed to remove unbound proteins, and the phosphorylated ligand is then eluted from the solid support.

Also provided is a method for treating a patient suffering from a proliferative cell disorder, comprising administering to said patient, an effective amount of the polypeptide of the present invention. Alternatively, the method may comprise explanting cells from the patient, transfecting the cells with a nucleic acid encoding a peptide comprising a non-SH2 PTB domain, selecting for cells which have incorporated said nucleic acid, and reimplanting the cells into the patient. Such proliferative cell disorders include, e.g., atherosclerosis, inflammatory joint disease, psoriasis, restinosis, and cancer.

BRIEF DESCRIPTION OF THE DRAWINGS

FIG. 4 shows a comparison of the amino acid sequences of SHC and SCK. Shown is a comparison of residues 11 to 432 of SHC (SEQ ID NO:3) with a SCK partial clone (SEQ ID NO:1). Bold, uppercase letters represent identical residues. The PTB domains of SHC (FIG. 2, Panel C) and SCK are enclosed in boxes (SEQ ID NO:4) and (SEQ ID NO:2), respectively; the SH2 domains are underlined. Asterisks mark a FLVRES-like sequence in the PTB domain. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIGS. 5A, 5B and 5C show the nucleotide sequence and deduced amino acid sequence of the partial SCK protein, including the PTB (SEQ ID NO:5) and (SEQ ID NO:6), respectively domain. The termini of the SCK PTB domain and the nucleotide sequence encoding that domain are indicated by the arrows (nucleotide position 100-651 as shown in the figure).

FIGS. 6A, 6B and 6C show the nucleotide sequence and deduced amino acid sequence of the SHC protein (SEQ ID NO:7) and (SEQ ID NO:8), respectively, including the 186 amino acid SHC PTB domain, corresponding to amino acid residues 46 to 232 of SHC that bind to pp145. The termini of the SHC PTB domain are indicated by the arrows (nucleotide position 136 through 693, as shown in the figure).

DESCRIPTION OF THE PREFERRED EMBODIMENT

I. General Description

A. SHC Protein

As discussed previously, the SHC gene encodes two transforming proteins that are tyrosine phosphorylated in response to a number of growth factors, and have been implicated as mediators of signaling from growth factor receptor and non-receptor tyrosine kinases to Ras.

The full length nucleotide sequence, and deduced amino acid sequences of the SHC gene have been previously described. See Pelicci et al., Cell 70:93–104 (1992). Furthermore, identified within this sequence were 1) an SH2 domain at the COOH-terminus, which binds tyrosine phosphorylated targets, such as activated growth factor receptors, 2) a region of similarity to human alpha-1 collagen in the middle of the molecule that contains a binding site for the GRB2 adapter protein, and 3) a 232-residue $NH_2$-terminus with previously unknown function. Surprisingly, however, it has now been discovered that within this $NH_2$-terminal region of the SHC protein is a domain which is capable of binding to tyrosine-phosphorylated proteins in a manner similar to that of the SH2 domains. This phosphotyrosine binding domain ("PTB") binds specifically to the tyrosine phosphorylated form of its target protein. Furthermore, the amino acid sequence of the phosphotyrosine binding domain ("PTB") is not similar to that of any member of the known SH2 domain family.

1. Analysis of SHC Binding

Figure 1:
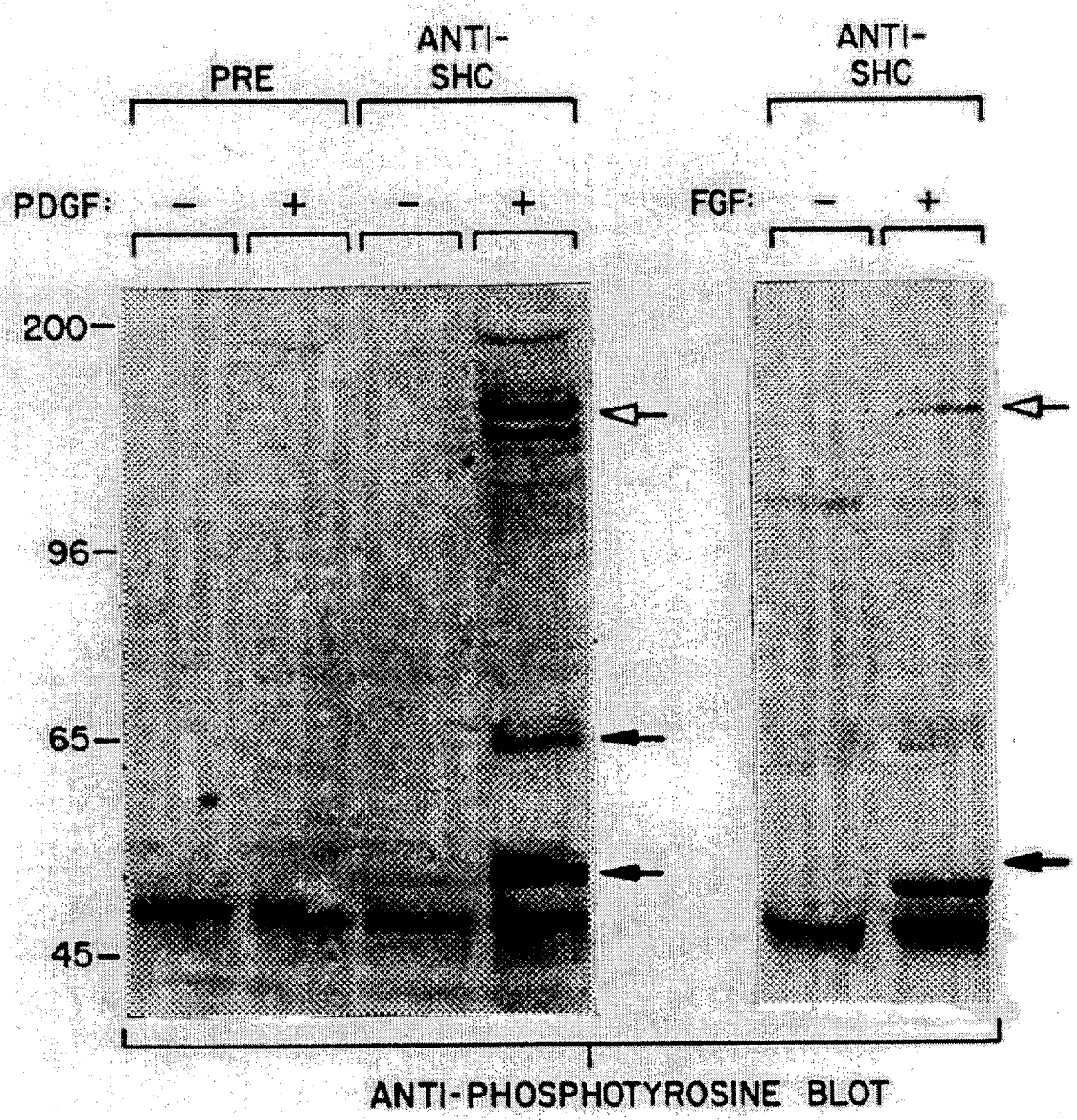
FIG. 1 is an immunoblot using antibody to phosphotyrosine. The blot illustrates the association of SHC with growth factor stimulated (PDGF and FGF) 145-kD tyrosine-phosphorylated proteins in vivo, immunoprecipitated with pre-immune serum ("PRE") or antiserum to SHC ("anti-SHC") and immunoblotted with antibody to phosphotyrosine. The black arrows indicate the 52-kD SHC protein and a 66-kD SHC-related protein seen in fibroblasts. The pp145 proteins are indicated by the open arrows. Each lane contains equal amounts of SHC as determined by immunoblotting with antiserum to SHC.

Identification of the PTB domain began with investigation of proteins that co-immunoprecipitated with the SHC protein in growth factor-stimulated cells. Several tyrosine-phosphorylated proteins of approximately 145 kD (collectively referred to as pp145) were present in anti-SHC immunoprecipitates from cells treated with either platelet-derived growth factor (PDGF) or fibroblast growth factor (FGF), but not in anti-SHC immunoprecipitates from unstimulated cells (FIG. 1). Similar tyrosine phosphorylated protein(s) were associated with SHC in B cells stimulated with antibodies to IgM, in activated T cells, in HepG2 hepatoma cells stimulated with interleukin 6 (IL6), and in CCE embryonic stem cells stimulated with leukemia inhibitory factor (LIF). The number and electrophoretic mobility of the pp145 proteins varied slightly among different cell types. These may represent different proteins or the same protein with different amounts of phosphorylation. All of these proteins appear to bind to SHC in a similar manner. The pp145 proteins in fibroblasts or in B cells were not recognized by immunoblotting with antibodies to SHC, phospholipase C gamma, Ras guanosine triphosphatase-activating protein (Ras GAP), the guanine nucleotide exchange factor Son-of-Sevenless (SOS), insulin receptor substrate 1 (IRS-1), the guanine nucleotide exchange factor C3G, the transforming protein eps15 or the PDGF or FGF receptors.

To characterize binding of SHC to pp145, proteins were separated from cell lysates by SDS-polyacrylamide gel electrophoresis (PAGE), transferred to nitrocellulose and incubated with $^{32}$P-labeled glutathione S-transferase (GST)-SHC fusion protein. $^{32}$P-labeled GST-SHC bound specifically to three proteins of approximately 180, 145 and 120 kD from lysates of PDGF-stimulated fibroblasts, but did not bind any proteins from lysates of unstimulated cells (FIG. 2, Panel A). The 180-kD band co-migrated with the autophosphorylated PDGF receptor; the 145-kD band co-migrated with the major pp145 protein identified in FIG. 1; the identity of the 120-kD protein is unknown. The $^{32}$P-GST-SHC probe also bound 145-kD proteins present in anti-SHC immunoprecipitates from PDGF-stimulated cells, but did not bind any proteins in immunoprecipitates from unstimulated cells (FIG. 2, Panel A). Therefore, the $^{32}$P-SHC probe apparently binds to the same 145-kD protein or proteins that associate with SHC in vivo. These experiments demonstrated that SHC binds pp145 directly, and that interaction of SHC and pp145 in vitro requires PDGF stimulation in vivo.

2. Deletional Analysis of SHC Protein

To map the region of the SHC protein responsible for binding to pp145, $^{32}$P-labeled GST-SHC probes were prepared containing deletions of various domains. Deletion of the SH2 domain of SHC eliminated binding to the p180 and p120 proteins in lysates of PDGF-stimulated cells but did not affect binding to pp145 in either cell lysates or in anti-SHC immunoprecipitates (FIG. 2, Panel B). Further, the isolated SHC SH2 domain bound to p180 and p120, but not to pp145 (FIG. 2, Panel B). Therefore, binding of SHC to p120 and p180 was due to the SH2 domain, but binding of SHC to pp145 did not require the SH2 domain. By further deletional analysis, a 186 amino acid fragment representing residues 46 to 232 of SHC that bound pp145 (FIG. 2, Panel C) was identified. This fragment bound specifically to pp145, and not to any other proteins in the nitrocellulose filter binding assays of lysates or anti-SHC immunoprecipitates from cells stimulated with PDGF, FGF, or from activated B cells. This region of the SHC protein also specifically bound pp145 in solution binding assays (FIG. 2, Panel D). The pp145-binding domain (hereafter referred to as "the PTB domain") is located in the $NH_2$-terminal portion of the SHC protein, for which no function had been previously assigned.

Figure 3A:
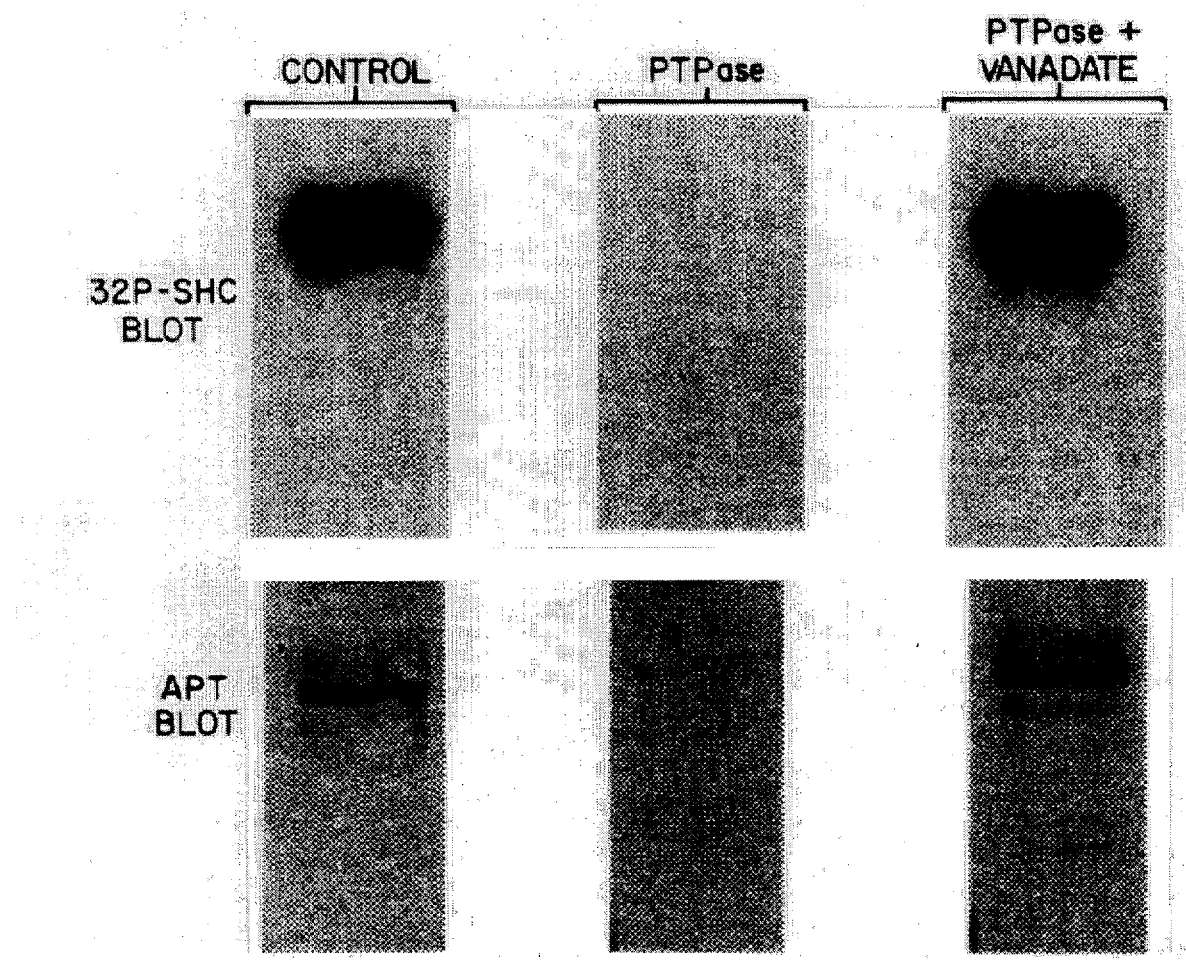
FIGS. 3A and 3B show the involvement of phosphotyrosine in binding of SHC to pp145. In Panel A, the proteins in anti-SHC immunoprecipitates from PDGF-stimulated fibroblasts were immobilized on nitrocellulose and treated with tyrosine-specific phosphatases ("PTPase") in the presence or absence of the PTPase inhibitor sodium orthovanadate ("PTPase+vanadate"). The filters were then blotted with $^{32}$P-labeled GST-SHC ("32P-SHC BLOT") (top) or immunoblotted with antibody to phosphotyrosine ("APT BLOT") (bottom). In Panel B, lysates from PDGF-stimulated cells were blotted with $^{32}$P-labeled GST-SHC in the presence of the indicated concentrations of phosphotyrosine ("P-TYR") or phosphoserine ("P-SER").
Figure 3B:
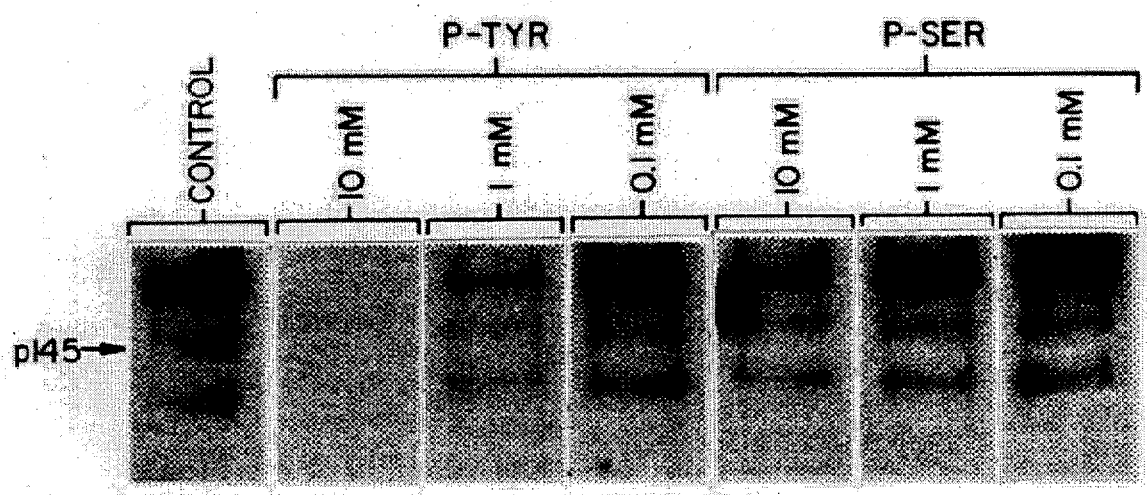

Because both SHC and pp145 are tyrosine phosphorylated in growth factor-stimulated cells, the binding properties of these two molecules, and how they were influenced by tyrosine phosphorylation was examined further. Phosphotyrosine was not detected on immunoblots of baculovirus-derived GST-SHC protein probe using antibody to phosphotyrosine, and treatment of the GST-SHC probe with tyrosine-specific phosphatases had no effect on binding to pp145. Therefore, tyrosine phosphorylation of SHC is not required for binding. To investigate the relationship of phosphorylation of pp145 to binding with SHC, pp145 derived from anti-SHC immunoprecipitates was transferred from PDGF-stimulated cells to nitrocellulose and treated with tyrosine-specific phosphatases. Dephosphorylation of immobilized pp145 completely eliminated binding to $^{32}$P-labeled GST-SHC (FIG. 3A). This effect was prevented by inclusion of the tyrosine phosphatase inhibitor sodium orthovanadate. Conversely, when pp145 from unstimulated cells, which should not bind SHC, was phosphorylated with recombinant PDGF receptor, the pp145 then bound to the PTB domain of the SHC protein SHC. Therefore, binding of SHC to pp145 requires pp145 to be tyrosine phosphorylated. To investigate the mechanism of PTB binding to pp145 further, proteins in cell lysates were separated by SDS-PAGE, transferred to nitrocellulose, and assayed for binding of $^{32}$P-labeled GST-SHC to pp145 in the presence of phosphotyrosine. Binding of GST-SHC to pp145 was competitively inhibited by high concentrations of phosphotyrosine, but not by similar concentrations of phosphoserine (FIG. 3B). Phosphotyrosine also inhibited binding of SHC to p180 and p120, which are SH2 domain-dependent interactions. These experiments suggested that binding of the PTB region to pp145 involves recognition of phosphotyrosine, as does SH2 domain binding.

Taken together, these results demonstrate that (i) the PTB domain of SHC specifically binds to pp145 and not to other proteins, (ii) that this interaction requires stimulation of cells by various growth factors, and (iii) that the PTB domain specifically recognizes the tyrosine-phosphorylated form of pp145. This combination of specificities is functionally similar to that of SH2 domains. It was also observed that pp145 could not be effectively dephosphorylated while it was complexed to SHC in immunoprecipitates. This suggested that the PTB domain protected the phosphotyrosine of pp145 from phosphatase action, as do SH2 domains (Birge et al., *J. Biol. Chem.* 267, 10588–10595 (1992)). However, PTB domains clearly have a different structure from SH2 domains. The amino acid sequence of the PTB region of SHC is different from all members of the known SH2 domain family. The only recognizable sequence similarity is a short motif present in the extreme $NH_2$-terminal end of the PTB domain, GVSYLVR, which is somewhat similar to the consensus sequence for phosphotyrosine binding in SH2 domains, G(S or T)FLVRES (FIG. 4) (SEQ ID NO:9)(Mayer et al., *Mol. Cell. Biol.* 12, 609 (1992)). However, mutation of the arginine in this motif (R55 of SHC) to leucine did not affect binding of the PTB domain to pp145, whereas the analogous mutation in SH2 domains eliminates binding to tyrosine phosphorylated targets (Marengere and Pawson *J. Biol. Chem.* 267, 22779–86 (1992); Bibbins et al., *Mol. Cell. Biol.* 13, 7278–87 (1993); S. Katzav *Oncogene*, 8, 1757–63 (1993)). The remainder of the PTB domain has little or no sequence similarity with highly conserved residues or motifs present in known SH2 domains, some of which are important for SH2 domain function. The predicted secondary structure of the PTB domain is also different from that of SH2 domains. Accordingly, it is apparent that the structural basis upon which PTB domain phosphotyrosine binding is based is markedly different from that of the known SH2 domains.

B. Identification of the Homologous SCK Protein

Comparison of the DNA sequence of the PTB domain with sequences in computer databases revealed a gene which contained a putative PTB domain. A partial clone of this gene, EST03775, was originally obtained by sequencing expressed sequence tags from human brain cDNA clones (Adams et al., *Nature Genetics* 4,256–267 (1993)), but had not been recognized as a putative signaling molecule. Specifically, only a 305 bp segment had been reported. By screening human placental and HepG2 cDNA libraries with EST03775, a larger partial clone encoding a protein with a PTB domain and a SH2 domain similar to those of SHC was identified, which is herein referred to as SCK (for ShC-liKe) (FIG. 4) (SEQ ID NO:1). The conserved region of the PTB domain correlated with the PTB domain which had bound to pp145. The identification of a PTB domain in SCK establishes that PTB domains are present in more than one gene. Northern blot analysis demonstrated that the tissue distribution of SCK mRNA is different from that of SHC. SCK mRNA expression is much higher in liver than in other tissues, and is present in brain. SHC mRNA expression is approximately the same in liver as in other tissues, except that it is very low in brain.

These data are consistent with a model in which stimulation of cells with growth factors leads to tyrosine phosphorylation of pp145, which then binds to SHC through its PTB domain. In this way, the PTB domain directs assembly of a signaling complex in the same way as does the SH2 domains of SHC or other signaling proteins. This signaling pathway is also referred to herein as the PTB domain/phosphorylated ligand regulatory system. Thus, pp145, a target of the SHC PTB domain, can also be an important signaling molecule. It has been proposed that SHC links growth factor receptor and non-receptor tyrosine kinases to activation of Ras; one mechanism for this link is formation of a complex of SHC with GRB2, an adapter protein, and with SOS, a guanine nucleotide exchange factor for Ras (Egan et al. *Nature*, 363,45–51 (1993)). Accordingly, pp145 can also participate in the regulation of Ras signaling by virtue of its association with SHC.

II. Polypeptides Comprising a PTB Domain

In one aspect, the present invention provides isolated polypeptides which are capable of binding a tyrosine-phosphorylated protein, through a non-SH2 PTB domain. Non-SH2 PTB domains are those protein domains which are capable of specifically binding tyrosine phosphorylated proteins, but comprise an amino acid sequence which is different from that found in the known SH2 sequences.

The terms "isolated" and "substantially pure" refer, interchangeably, to proteins, polypeptides and nucleic acids which are separated from proteins, or contaminants with which they are naturally associated. A protein or polypeptide is isolated when that protein makes up greater than about 50% of the total protein content of the composition containing that protein, typically, greater than about 60% of the total protein content. More typically, a substantially pure protein will make up from about 75 to about 90% of the total protein. Preferably, the protein will make up greater than about 90%, and more preferably, greater than about 95% of the total protein in the composition.

Isolation and purification of the polypeptides of the present invention can be carried out by methods that are well known in the art. For example, the polypeptides may be purified using readily available chromatographic methods, e.g., ion exchange, hydrophobic interaction, HPLC or affinity chromatography to achieve desired purity. Affinity chromatography can be particularly attractive in allowing the investigator to take advantage of the specific activity of the desired polypeptide, e.g., phosphotyrosine binding.

Exemplary polypeptides will have an amino acid sequence which is substantially homologous to the amino acid sequence of the SHC PTB domain, or phosphotyrosine binding fragments thereof. The phrase "PTB domain" as used herein refers to a polypeptide domain which has an amino acid sequence that is substantially homologous to the amino acid sequence of the SHC non-SH2 phosphotyrosine binding domain. This SHC non-SH2 domain consists of amino acid residues 46 through 232 of the SHC protein amino acid sequence. Also included are sequences which comprise the SCK protein's PTB domain.

By substantially homologous is meant an amino acid sequence which is at least about 50% homologous to the SHC PTB domain, preferably at least about 90% homologous, and more preferably at least about 95% homologous. Examples of preferred polypeptides are those derived from the SHC or SCK proteins, and having the sequence as shown in FIG. 4, for the SCK and SHC PTB (SEQ ID NO:2) and (SEQ ID NO:4), respectively domains (or FIGS. 5A to C and 6A to C, respectively)(SEQ ID NO:6 and SEQ ID NO:8), or phosphotyrosine binding fragments thereof. Thus, included within the present invention are amino acid variants of the SHC and SCK PTB domain sequences, provided those variants retain the ability to bind tyrosine phosphorylated proteins. These variants may include insertions, deletions and substitutions with other amino acids. Glycosylation modifications, either changed, increased amounts or decreased amounts, as well as other sequence modifications are envisioned. Thus the amino acid variants of these polypeptides, e.g., analogs, will generally be substantially equivalent to the amino acid sequence of either the SHC or SCK PTB domain.

Polypeptides of the present invention may also be characterized by their ability to bind antibodies raised against the PTB domains shown in FIG. 4. These antibodies recognize polypeptide domains that are homologous to the PTB domain. Homologous domains encompass the family of PTB domains, but do not include other phosphotyrosine binding domains, such as SH2 domains. A variety of immunoassay formats may be used to select antibodies specifically immunoreactive with a particular protein or domain. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity. Antibodies to PTB domains and polypeptides comprising PTB domains are discussed in greater detail, below.

Phosphotyrosine binding fragments of the above peptides may be identified and prepared by methods well known in the art. For example, selective proteolytic digestion, recombinant deletional methods, or peptide synthesis methods may be employed to identify the specific fragments which are capable of phosphotyrosine binding. See, e.g., Sambrook et al. Typically, such fragments will comprise fewer than about 50 amino acids, more typically, they will comprise fewer than about 20 amino acids, and preferably they will comprise from about 6 to about 15 amino acids.

It may also be desirable to provide the polypeptides of the present invention free of phosphotyrosine binding domains other than the PTB domain. For example, where it is desired to focus only upon PTB domain binding, and the target protein possesses numerous different phosphorylated tyrosine residues. In this case, deletional peptides lacking other phosphotyrosine binding domains, e.g., SH2 domains, may be prepared by recombinant DNA techniques well known in the art.

The polypeptides of the present invention may be used as isolated polypeptides, or may exist as fusion proteins. A "fusion protein" generally refers to a composite protein made up of two separate, heterologous proteins which are normally not fused together as a single protein. Thus, a fusion protein may comprise a fusion of two similar and homologous sequences, provided these sequences are not normally fused together. Fusion proteins will generally be made by either recombinant nucleic acid methods, i.e., as a result of transcription and translation of a gene fusion comprising a segment encoding a polypeptide comprising the PTB domain and a segment which encodes one or more heterologous proteins, or by chemical synthesis methods well known in the art.

These fusion proteins may be prepared to exhibit a combination of properties or activities of the derivative proteins. Typical fusion proteins may include a polypeptide comprising the PTB domain fused to a reporter polypeptide, e.g., a substrate, cofactor, inhibitor, affinity ligand, antibody binding epitope tag, or an enzyme which is capable of being assayed. Because of its ability to recognize and bind specific tyrosine phosphorylation sites in a protein, the PTB domain may act as an affinity ligand to direct the activity of the fused protein directly to tyrosine phosphorylated proteins. In the case of a reporter peptide\PTB domain fusion, this allows the presence and or location of tyrosine phosphorylated proteins which bind the PTB domain to be easily determined. Alternatively, fusion proteins may facilitate isolation and identification of the polypeptides comprising the PTB domain, by providing an easily purifiable hybrid protein, i.e., the polypeptide fused to an affinity ligand, or antibody binding epitope which may then be purified using well known affinity purification methods, or detected. Examples of such affinity ligands and antibody binding epitopes may include, e.g., influenza virus hemagglutinin (IHA) epitope tag, or glutathione-S-transferase. Other typical fusion partners include bacterial β-galactosidase, trpE, protein A, β-lactamase, α-amylase, alcohol dehydrogenase and yeast αmating factor. See, e.g., Godowski et al., *Science* 241:812–816 (1988).

The polypeptides of the present invention may be prepared by a variety of means, e.g., recombinant or synthetic. In general, techniques for recombinant production of proteins are described, for example, in Sambrook et al., *Molecular Cloning: A Laboratory Manual* (2nd ed.) Vols. 1–3, Cold Spring Harbor Laboratory, (1989). Techniques for the synthesis of polypeptides are generally described in Merrifield *J. Amer. Chem. Soc.* 85:2149–2456 (1963), Atherton et al., *Solid Phase Peptide Synthesis: A Practical Approach*, IRL Press, Oxford (1989), and Merrifield, *Science* 232:341–347 (1986).

III. Nucleic Acids Encoding Polypeptides Comprising a PTB Domain and Cells Capable of Expressing Same Also provided in the present invention are isolated nucleic acid sequences that encode polypeptides which comprise a non-SH2 PTB domain. Preferably, such nucleic acid sequences will comprise a segment that is substantially homologous to the nucleotide sequence encoding the SHC or SCK PTB domains. More preferred are those nucleic acid sequences, shown in FIGS. 5A–C and 6A–C, which comprise the nucleotide sequence encoding the SCK or SHC PTB domain, respectively.

Substantial homology in the nucleic acid context means that the segments, or their complementary strands, when compared, are the same when properly aligned, with the appropriate nucleotide insertions or deletions, in at least about 60% of the nucleotides, typically, at least about 70%, more typically, at least about 80%, usually, at least about 90%, and more usually, at least about 95% to 98% of the nucleotides. Alternatively, substantial homology exists when the segments will hybridize under selective hybridization conditions to a strand, or its complement, typically using a sequence of at least about 20 contiguous nucleotides derived from the SHC or SCK nucleotide sequence. However, larger segments will usually be preferred, e.g., at least about 30 contiguous nucleotides, more usually about 40 contiguous nucleotides, and preferably more than about 50 contiguous nucleotides. Selective hybridization exists when hybridization occurs which is more selective than total lack of specificity. See, Kanehisa, *Nucleic Acid Res.* 12:203–213 (1984).

Nucleic acids of the present invention include RNA, cDNA, genomic DNA, synthetic forms and mixed polymers, both sense and antisense strands. Furthermore, different alleles of each isoform are also included. The present invention also provides recombinant nucleic acids which are not otherwise naturally occurring. The nucleic acids included in the present invention will typically comprise RNA or DNA or mixed polymers. The DNA compositions will generally include a coding region which encodes a polypeptide comprising an amino acid sequence substantially homologous to the amino acid sequence of the SHC PTB domain. More preferred are those DNA segments comprising a nucleotide sequence as shown in FIGS. 5A–C and 6A–C, which encodes the SCK or SHC PTB domains, respectively.

CDNA encoding the polypeptides of the present invention, or fragments thereof, may be readily employed as a probe useful for obtaining genes which encode the PTB containing polypeptides of the present invention. Typical nucleic acid probes may be prepared from the amino acid sequences of the SHC or SCK PTB domain. In particular, probes may be prepared based upon segments of the amino acid sequence which possess relatively low levels of degeneracy, i.e., few or one possible nucleic acid sequences which encode therefor. Suitable synthetic DNA fragments may then be prepared, e.g., by the phosphoramidite method described by Beaucage and Carruthers, *Tetre. Letts.* 22:1859–1862 (1981). Alternatively, nucleotide sequences which are relatively conserved among the SHC and SCK PTB domain coding sequences may be used as suitable probes. A double stranded probe may then be obtained by either synthesizing the complementary strand and hybridizing the strands together under appropriate conditions or by adding the complementary strand using DNA polymerase with an appropriate primer sequence. Such cDNA probes may be used in the design of oligonucleotide probes and primers for screening and cloning such genes, e.g., using well known PCR techniques. Such nucleic acids, or fragments may comprise part or all of the cDNA sequence that encodes the polypeptides of the present invention. Effective cDNA probes may comprise as few as 15 consecutive nucleotides in the cDNA sequence, but will often comprise longer segments. Further, these probes may further comprise an additional nucleotide sequence, such as a transcriptional primer sequence for cloning, or a detectable group for easy identification and location of complementary sequences.

cDNA or genomic libraries of various types may be screened for new alleles or related sequences using the above probes. The choice of cDNA libraries normally corresponds to tissue sources which are abundant in mRNA for the desired polypeptides. Phage libraries are normally preferred, but plasmid libraries may also be used. Clones of a library are spread onto plates, transferred to a substrate for screening, denatured, and probed for the presence of the desired sequences.

The nucleic acids of the present invention may be present in whole cells, cell lysates or in partially pure or substantially pure or isolated form. Such "substantially pure" or "isolated" forms of these nucleic acids generally refer to the nucleic acid separated from contaminants with which it is generally associated, e.g., lipids, proteins and other nucleic acids. The nucleic acids of the present invention will be greater than about 50% pure. Typically, the nucleic acids will be more than about 60% pure, more typically, from about 75% to about 90% pure, and preferably, from about 95% to about 98% pure.

The present invention also includes fragments of the above described nucleic acids. Such fragments will generally comprise a segment of from about 15 to about 150 nucleotides. These fragments can be useful as oligonucleotide probes in the methods of the present invention, or alternatively to encode phosphotyrosine binding polypeptide fragments of the PTB domain as also described herein. Also provided are substantially similar nucleic acid sequences, allelic variations and natural or induced sequences of the above described nucleic acids. Also included are chemically modified and substituted nucleic acids, e.g., those which incorporate modified nucleotide bases or which incorporate a labelling group.

In addition to comprising a segment which encodes a polypeptide containing a PTB domain, the nucleic acids of the present invention may also comprise a segment encoding a heterologous protein, such that the gene is expressed to produce the two proteins as a fusion protein, as substantially described above.

In addition to their use as probes, the nucleic acids of the present invention may also be used in the preparation of the polypeptides of the present invention, namely those polypeptides comprising the non-SH2 PTB domain.

DNA encoding the polypeptides of the present invention will typically be incorporated into DNA constructs capable of introduction to and expression in an in vitro cell culture. Often, the nucleic acids of the present invention may be used to produce a suitable recombinant host cell. Specifically, DNA constructs will be suitable for replication in a unicellular host, such as bacteria, e.g., *E. coli*, but may also be intended for introduction into a cultured mammalian, plant, insect, or other eukaryotic cell lines. DNA constructs prepared for introduction into bacteria or yeast will typically include a replication system recognized by the host, the intended DNA segment encoding the desired polypeptide, transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence; DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See, e.g., Sambrook et al., *Molecular Cloning: A Laboratory Manual* (2d ed.), vols. 1–3 Cold Spring Harbor Laboratory (1989). The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al., (1989).

Conveniently available expression vectors which include the replication system and transcriptional and translational regulatory sequences together with the insertion site for the PTB polypeptide encoding segment may be employed. Examples of workable combinations of cell lines and expression vectors are described in Sambrook et al., and in Metzger et al., *Nature* 334:31–36 (1988). For example, where an insect host cell is selected as the host cell of choice to express the polypeptide, the cDNA encoding the polypeptides of the invention may be cloned into a baculovirus expression vector (pV-IKS). The recombinant baculovirus may then be used to transfect a suitable insect host cell, e.g., Sf9 cells, which may then express the polypeptide. See, e.g., D. K. Morrison et al., *Cell* 58:649–657 (1989), M. D. Summers and G. E. Smith, *A Manual of Methods for Baculovirus Vectors and Insect Cell Culture Procedures*, Texas Agricultural Station, College Station, Tex. (1987).

The vectors containing the DNA segments of interest, e.g., those encoding polypeptides comprising the non-SH2 PTB domain, can be transferred into the host cell by well known methods, which may vary depending upon the type of host used. For example, calcium chloride transfection is commonly used for prokaryotic cells, whereas calcium phosphate treatment may be used for other hosts. See, Sambrook et al. The term "transformed cell" as used herein, includes the progeny of originally transformed cells.

IV. Proteins That Bind PTB

Also provided by the present invention are tyrosine phosphorylated proteins which are specifically recognized by the PTB domain. Such proteins are generally produced in response to cell activation, e.g., growth factor activation, and may be identified by their ability to specifically bind the PTB domain. Accordingly, identification and characterization of these proteins can advance the understanding, characterization and manipulation of cell signaling pathways in general.

Specifically provided is an isolated polypeptide having an approximate molecular weight of 145 kD. This polypeptide is derived from activated cells. Activated cells refer to mammalian cells, including fibroblasts, myoblasts, B-cells and T-cells of human and nonhuman origin. These cells are generally activated by growth factors, e.g., PDGF, FGF, EGF, insulin and insulin-like growth factors; cytokines and lymphokines, e.g., interleukins; and antibodies and ligands to receptors involved in growth regulation and cell division. Examples of specific activated cells include, e.g., PDGF activated fibroblasts, such as Balb/c 3T3 cells, FGF activated myoblasts, such as L6 cells, antibody activated B-cells, IL-6 activated hepatoma cells, such as the HepG2 cell line and leukemia inhibitory factor stimulated embryonic stem cells, such as CCE stem cells. This polypeptide is characterized by phosphorylation of one or more tyrosine residues upon activation of a cell, as described above. Further, this protein does not bind an isolated SHC SH2 domain, but will bind polypeptides having the amino acid sequence of the SHC PTB domain. Isolation and purification of these proteins may be carried out by known methods, e.g., ion exchange, HIC, affinity chromatography, HPLC, and the like.

As a specific signal of growth factor activation of cells, this protein provides an ideal target for the non-SH2 PTB binding in the screening methods of the present invention.

V. Antibodies

The polypeptides of the present invention, or fragments thereof will be useful in producing antibodies, either polyclonal or monoclonal. These antibodies are produced by immunizing an appropriate vertebrate host, e.g., mouse or rabbit, with the polypeptide or fragment, alone or in conjunction with an adjunct. Usually, two or more immunizations are involved, and a few days following the last injection, the blood or spleen of the host will be harvested.

For production of polyclonal antibodies, an appropriate target immune system is selected, typically a mouse or rabbit, but including goats, sheep, cows, guinea pigs and rats. The substantially purified antigen is presented to the immune system in a fashion determined by methods appropriate for the animal. These and other parameters are well known to immunologists. Typically, injections are given in the footpads, intramuscularly, intradermally or intraperitoneally. The immunoglobulins produced by the host can be precipitated, isolated and purified by routine methods, including affinity purification.

For monoclonal antibodies, appropriate animals will be selected and the desired immunization protocol followed. After the appropriate period of time, the spleens of these animals are excised and individual spleen cells are fused, typically, to immortalized myeloma cells under appropriate selection conditions. Thereafter, the cells are clonally separated and the supernatants of each clone are tested for the production of an appropriate antibody specific for the desired region of the antigen. Techniques for producing antibodies are well known in the art. See, e.g., Goding et al., *Monoclonal Antibodies: Principles and Practice* (2d ed.) Acad. Press, N.Y., and Harlow and Lane, *Antibodies: A Laboratory Manual*, Cold Spring Harbor Laboratory, New York (1988). Other suitable techniques involve the in vitro exposure of lymphocytes to the antigenic polypeptides or alternatively, to selection of libraries of antibodies in phage or similar vectors. Huse et al., Generation of Large Combinatorial Library of the Immunoglobulin Repertoire in Phage Lambda, *Science* 246:1275–1281 (1989). Monoclonal antibodies with affinities of $10^8$ liters/mole, preferably $10^9$ to $10^{10}$ or stronger, will be produced by these methods.

The antibodies generated can be used for a number of purposes, e.g., as probes in immunoassays, for inhibiting PTB binding to its target tyrosine phosphorylated proteins, in diagnostics or therapeutics, or in research to further elucidate the functioning of the signaling pathways in activation of cells by growth factors, hormones, cytokines or the like.

The antibodies of the present invention can be used with or without modification. Frequently, the antibodies will be labelled by joining, either covalently or non-covalently, a substance which provides for a detectable signal. Such labels include those that are well known in the art, such as those as described previously for the polypeptides of the invention.

Preferred antibodies are those which specifically recognize polypeptides which comprise a phosphotyrosine binding domain which is non-SH2. More preferred are those antibodies which bind to polypeptides having an amino acid sequence substantially homologous to the amino acid sequence of SHC PTB domain. Still more preferred are those antibodies which bind to polypeptides comprising the amino acid sequence of the SHC or SCK PTB domains.

VI. Methods for Use

A. Diagnostics and Screening

As noted above, the polypeptides comprising the PTB domain may be particularly useful as affinity ligands capable of binding tyrosine phosphorylated proteins. Further, tyrosine phosphorylation of proteins is a common signal in cellular functioning. Accordingly, the polypeptides of the present invention may find a variety of uses in research, as well as diagnostic and therapeutic applications.

For example, the polypeptides comprising the PTB domain may generally be useful in methods for identifying tyrosine phosphorylated proteins. Such methods may allow for the identification of proteins involved in signaling pathways, such as cell activation following the binding of a ligand to a cell surface receptor. Specifically, these methods are useful in identifying downstream signals following growth factor, hormone, antibody and cytokine activation of cells.

In one aspect, one may use the polypeptides of the present invention to detect whether a protein is capable of binding the PTB domain, that is, whether the protein is tyrosine phosphorylated in the first instance. Detection of tyrosine phosphorylated proteins using the polypeptides of the present invention may be accomplished by a number of means. For example, in some instances, it may be useful to immobilize the protein to be tested upon a solid support, e.g., a microtiter well, or nitrocellulose membrane. After blocking of remaining groups on the support, the protein to be tested may be exposed to an appropriate amount of the labelled polypeptide containing the PTB domain, as described herein. Detection of the label bound to the test protein indicates that the protein is tyrosine phosphorylated. As a specific example, following SDS-PAGE, the gel may be electroblotted onto an appropriate solid support, e.g., a nitrocellulose or PVDF membrane. Remaining unbound regions of the membrane may then be blocked with an appropriate inert protein, e.g., bovine serum albumin. Following buffer rinses, the blot is then contacted with a polypeptide comprising a PTB domain and a detectable group, e.g., a radiolabel or enzyme. Radiographs of the blot may be compared to simultaneously run, stained SDS-PAGE gels, and the radiolabel bound proteins may be identified. Specific methods for SDS-PAGE, electroblotting, and radiograph exposures are very well known in the art.

Alternatively, the methods of the present invention may be applied to detect the presence, absence, increase or decrease in the level of tyrosine phosphorylated protein in vitro or in vivo. The ability to detect signals of cellular functioning allows for the screening of compounds which affect that functioning. For example, by detecting the increase or decrease in the level of tyrosine phosphorylated proteins in response to contact with a particular compound, one can determine whether the compound is an agonist or antagonist of a cellular function which results in that tyrosine phosphorylation of proteins in vivo.

To assay for compounds that act as agonists or antagonists of functions which result in tyrosine phosphorylation, cells are exposed to known agonists, known antagonists, and/or test compounds which may be, or may contain, agonists or antagonists. An agonist, antagonist, or test compound may be a chemical compound, a mixture of chemical compounds, a biological macromolecule, or an extract made from biological materials such as bacteria, plants, fungi, or animal cells or tissues. Test compounds are evaluated for potential activity as agonists or antagonists of functions which result in tyrosine phosphorylation by inclusion in screening assays described herein. An "agonist" will enhance the level of tyrosine phosphorylated proteins in an activated cell, while an "antagonist" will diminish the level of tyrosine phosphorylated proteins. The terms "agonist" and "antagonist", as used herein, do not imply a particular mechanism of function.

For many of the methods of the present invention, the polypeptides and nucleic acids of the invention may be covalently attached or linked to a detectable group to facilitate screening and detection. Useful detectable groups, or labels, are generally well known in the art. For example, a detectable group may be a radiolabel, such as, $^{125}I$, $^{32}P$ or $^{35}S$, or a fluorescent or chemiluminescent group. Alternatively, the detectable group may be a substrate, cofactor, inhibitor, affinity ligand, antibody binding epitope tag, or an enzyme which is capable of being assayed. Suitable enzymes include, e.g., horseradish peroxidase, luciferase, or another readily assayable enzymes. These enzyme groups may be attached to the PTB containing polypeptide by chemical means or expressed as a fusion protein, as already described.

In a specific aspect, a method is provided for determining whether a compound is an agonist or antagonist of a cellular activation signaling pathway. For these embodiments, the test compound to be screened may be incubated with activatable cells, which are characterized by their activation of tyrosine kinases, and thus, tyrosine phosphorylation of proteins, upon activation. Specific examples of these cells include PDGF activated fibroblasts, FGF activated myoblasts, such as L6 cells, antibody activated B-cells, activated T-cells, IL-6 activated hepatoma cells, such as the HepG2 cell line and leukemia inhibitory factor stimulated embryonic stem cells, such as CCE stem cells.

Following exposure to the activating agent, i.e., a growth factor, the cells are lysed, and the polypeptides of the present invention comprising the PTB domain may be used to assay the cell lysate for an increase or decrease in the level of tyrosine phosphorylated proteins in the cell in response to activation in the presence of the test compound. Preferably, the lysate may be assayed for the presence of pp145. Methods for preparation of a cell lysate are well known in the art (see, e.g., Methods in Enzymology Vol. 198, supra). Typically, cells are homogenized in the presence of buffers (e.g., Tris-HCl, HEPES), nonionic detergents (e.g., Tween-20; Triton X-100), and protease inhibitors (e.g., PMSF, aprotinin, leupeptin). Other inhibitors, such as phosphatase inhibitors (e.g., orthovanadate), may also be desirable. Typically conditions are chosen that are nondenaturing to the cellular proteins of interest. A preferred method for preparation of a cell lysate is by addition of lysis buffer (20 mM Tris-HCl, pH 7.3, 150 mM NaCl, 1% Triton X-100, 1 mM PMSF, 1 mM sodium orthovanadate, 10 µg/ml aprotinin and 10 µg/ml leupeptin) followed by cell disruption (e.g., by shaking or scraping). Usually, when preparing a cell lysate the insoluble matter in the cell lysate is removed by centrifugation (e.g., 10,000×g for 15 min.) and the clarified supernatant is recovered. Where exposure to the compound results in an increase or decrease in the level of tyrosine phosphorylated proteins in response to cell activation, when compared to an appropriate control, it is indicative that the compound may be an agonist or antagonist of a cell activation signaling pathway, respectively.

The amount or concentration of agonist/antagonist added will, when known, vary depending on the compound, but will generally range from about 10 pM to 100 µM. Typically, a variety of concentrations will be used. In the case of uncharacterized test compounds it may not be possible, and it is not necessary, to determine the concentration of agonist/antagonist.

It will also be desirable to include various experimental controls in the assay. Examples of appropriate controls include negative controls and positive controls. In testing for agonist activity, negative controls can include incubation of cells with inert compounds (i.e., compounds known not to have agonist activity) or in the absence of added compounds. Positive controls can include incubation of cells with compounds known to have agonist activity (e.g., the natural ligand). Logically similar (though complementary) controls can be included in assays for antagonist activity, as will be apparent to one of ordinary skill in the art of biology, as will be various additional controls. The description of controls is meant to be illustrative and in no way limiting.

More narrowly, the polypeptides of the present invention can be used as a model in vitro system for determining whether a compound is an agonist or antagonist of the binding of the PTB domain to its phosphorylated ligand. "Phosphorylated ligand" refers to a protein or polypeptide which is capable of interacting with the PTB domain to form a complex, e.g., tyrosine phosphorylated proteins such as pp145, or fragments thereof. These methods comprise providing a polypeptide comprising the PTB domain, and the phosphorylated ligand capable of interacting with the PTB domain, e.g., tyrosine phosphorylated proteins, such as pp145, to form a complex. The complex may then be incubated with a test compound. Binding between the PTB domain and the ligand may then be determined. An increase or decrease in the level of binding between the phosphorylated ligand and the polypeptide of the invention (comprising the PTB domain) in response to a particular compound would indicate that the compound is an agonist or antagonist of that binding, respectively. In some cases, it may be desirable to preincubate the phosphorylated ligand with the test compound, prior to introduction of the polypeptide comprising the PTB domain. The duration and conditions of preincubation will generally vary depending upon the compound being tested. Generally, this preincubation may be from about 5 minutes to about 1 hour. Further, the pH and temperature of the preincubation will generally correspond to the pH and temperature which are most effective for PTB domain binding to the protein. Accordingly, these conditions will likely reflect the conditions normal to the particular cell-line from which the PTB domain was derived.

It may also be desirable to provide the tyrosine phosphorylated ligand or polypeptide comprising the PTB domain immobilized upon a solid support, to facilitate screening of test compounds. Examples of suitable solid supports include agarose, cellulose, dextran, Sephadex, Sepharose, carboxymethyl cellulose, polystyrene, filter paper, nitrocellulose, ion exchange resins, plastic films, glass beads, polyaminemethylvinylether maleic acid copolymer, amino acid copolymer, ethylene-maleic acid copolymer, nylon, silk, etc. The support may be in the form of, e.g., a test tube, microtiter plate, beads, test strips, or the like. The reaction of the polypeptide or phosphorylated ligand with the particular solid support may be carried out by methods well known in the art.

In the case of a microtiter plate, the test compound may be added to the well of the microtiter plate to preincubate with the tyrosine phosphorylated protein. The polypeptide comprising the PTB domain may then be added to the microtiter well, and binding of the PTB domain to the protein may be assessed, e.g., by detection of detectable groups. The level of binding may then be compared to suitable positive and negative controls. Alternatively, by providing the polypeptide containing the PTB domain, and/or the phosphorylated ligand in known concentrations, one can assay for free, or unbound PTB domain and/or phosphorylated ligand, and by negative implication, determine the level of PTB domain/phosphorylated ligand complex which is formed.

Additionally, as an affinity ligand, the polypeptides comprising the PTB domain may also be useful in the purification of tyrosine phosphorylated proteins from a mixture of different proteins. Affinity purification of tyrosine phosphorylated proteins may be carried out using general affinity purification methods well known in the art. For example, the polypeptide of the present invention may be attached to a suitable solid support. Suitable solid supports include those generally well known in the art, e.g., cellulose, agarose, polystyrene, divinylbenzene and the like. Many suitable solid supports are commercially available from, e.g., Sigma Chemical Co., St Louis, Mo., or Pharmacia, Uppsala, Sweden, and come prepared for immediate coupling of affinity ligands.

The mixture of proteins may be contacted with the polypeptide bound to the solid support, such that the polypeptide selectively binds the tyrosine phosphorylated proteins within the mixture of proteins. The bound protein can then be washed to eliminate unbound proteins. Finally, substantially pure tyrosine phosphorylated protein may be eluted from the solid support by generally known elution protocols, e.g., washing with an excess of phosphotyrosine, which will compete with the binding of PTB to its target protein.

Alternatively, the non-SH2 PTB domain polypeptides of the present invention may be useful in modelling small molecules which interfere with PTB binding in vivo. In particular, the structure of the PTB domain, and more specifically, the actual phosphotyrosine binding site, from the known amino acid sequence and the 3-dimensional structure, which may be determined by x-ray crystallographic methods known in the art, may be applied in generating synthetic analogs and mimics of the particular PTB domain and, more specifically, the precise phosphotyrosine binding site. Synthetic elements may be pieced together based upon their analogy to the structural and chemical aspects of the PTB domain. Such mimics and analogs may be used in blocking or inhibiting specific aspects of the cell signaling pathways, e.g., growth factor activation, and may thus be useful as therapeutic treatments according to the methods described herein.

B. Therapeutics

In addition to the above described uses, the polypeptides and nucleic acids of the present invention may also be used in therapeutic applications for the treatment of human or non-human mammalian patients.

As a specific example, the polypeptides of the present invention may be used to inhibit or block the growth factor dependent activation or stimulation of cells, or more specifically, inhibit or block growth factor initiated mitogenesis. These methods may generally be used in the treatment of a variety of proliferative cell disorders, or in screening compounds effective for such treatment. "Proliferative cell disorder" refers generally to disorders which are characterized by excessive stimulation or activation of the mitogenic signaling pathways resulting in excessive or abnormal cell growth and/or differentiation. Specific disorders include, e.g., atherosclerosis, inflammatory joint diseases, psoriasis, restinosis following angioplasty, and cancer. The methods and compositions of the present invention may be particularly useful in the case of cancers where there are deregulated tyrosine kinases, such as thyroid, breast carcinoma, stomach cancer and neuroblastoma. Alternatively, the methods and compositions may be useful as prophylactic treatment, or in screening for compounds effective in prophylactic treatments. Such prophylactic treatments will generally be administered to inhibit or block "normal" cell proliferation, for example, in immunosuppression to prevent graft rejection, and to alleviate allergic responses involving mast cell activation.

Along this line, it can be appreciated that phosphotyrosine binding analogs of the polypeptides of the present invention may also be effective in blocking growth factor dependent activation. Specifically, synthetic analogs to the phosphotyrosine binding site, as described previously, of the polypeptides of the present invention may also be applied in the treatments described herein.

The quantities of reagents necessary for effective therapy, also referred to herein as an "effective amount," or "therapeutically effective amount," will depend upon many different factors, including means of administration, target site, physiological state of the patient and other medicants administered. Thus, treatment doses will need to be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Generally, therapeutically effective amounts of the PTB domain containing polypeptides of the present invention will be from about 0.0001 to about 100 mg/kg, and more usually, from about 0.001 to about 0.1 mg/kg of the host's body weight. Various considerations are described, e.g., in Gilman et al., (Eds.), *Goodman and Gilman's: The Pharmacological Basis of Therapeutics*, (8th ed. 1990), Pergamon Press, and *Remington's Pharmaceutical Sciences* (7th ed. 1985) Mack Publishing Co., Easton, Pa. Methods of administration, also discussed in the above references, include, e.g., oral, intravenous, intraperitoneal or intramuscular administration, and local administration, including topical, transdermal diffusion and aerosol administration, for therapeutic, and/or prophylactic treatment. The active agent, i.e., the PTB domain containing polypeptide, will generally be administered in a composition additionally comprising a pharmaceutically acceptable carrier. Pharmaceutically acceptable carriers will include water, saline, buffers and other compounds described in, e.g., the Merck Index, Merck and Co., Rahway, N.J.

Constituents of pharmaceutical compositions, in addition to the active agents, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline and the like. Additionally, these compositions may include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

Administration may also be carried out by way of a controlled release composition or device, whereby a slow release of the active ingredient allows continuous administration over a longer period of time.

Additionally, because tyrosine phosphorylation, and consequently phosphotyrosine binding, plays an important role in cell signaling pathways, the present invention can provide an exogenous regulatory mechanism in the treatment of these disorders. In particular, the treatment of a particular disorder may comprise gene therapy techniques involving the mutation or dysregulation of a particular PTB domain/ phosphorylated ligand regulatory scheme. For example, in the treatment of diseases associated with excessive activity of this regulatory scheme, the methods of the present invention may be applied in reducing that activity. Such a reduction of this activity may involve mutation of genes encoding PTB domains, and/or their phosphorylated ligands. Alternatively, gene therapy techniques may involve the introduction into afflicted cells, of genes which encode a PTB domain. This exogenously introduced PTB domain may compete with the overactive or over expressed PTB containing proteins, thus down regulating the regulatory schemes with which they are associated.

Strategies for gene therapy are reviewed in Friedmann, *Science* 244:1275 (9189). Genetic constructs encoding the PTB domain or functional derivative of that domain, can be used in these gene therapy techniques. Delivery of the genetic construct of interest, i.e., the nucleic acid encoding a non-SH2 PTB domain polypeptide, may be accomplished in vivo by administering the therapy vector to an individual patient, typically by systemic administration (e.g., intravenous, intraperitoneal, intramuscular, subdermal, or intracranial administration). Alternatively, the vector may be used to deliver nucleic acids to cells ex vivo, such as cells explanted from an individual patient or universal donor hematopoietic stem cells, neurons, etc, e.g., by transfection of the cells with nucleic acids of interest cloned into retroviruses. Following transfection, the cells are reimplanted into the patient, usually after selection for cells which have incorporated the nucleic acid. The infusion into the patient of transfected cells can replace cells which are dysfunctional for the particular regulatory scheme which results in the disorder being treated.

The present invention is further illustrated by the following examples. These examples are merely to illustrate aspects of the present invention and are not intended as limitations of this invention.

EXAMPLES

A. In Vivo Association of SHC with PP145 Proteins

Balb/c 3T3 cells, or L6 myoblasts expressing the human FGF receptor 1 [D. E. Johnson, P. L. Lee, J. Lu, L. T. Williams *Mol. Cell. Biol.* 10, 4728 (1990)], were grown to confluence in Dulbecco's modified Eagle medium containing bovine calf serum (10%), antibiotics, and for L6 cells, 800 µg/ml G418. Cells were stimulated at 37° C. for 10 min with either BB PDGF (2 nM) or basic FGF (25 ng/ml) and lysed at 4° C. in 1 ml/$10^6$ cells of lysis buffer [20 mM Tris-HCL (pH 8.0), 137 mM NaCl, 10% glycerol, 1% Triton X-100, 1 mM sodium orthovanadate, 100 mM NaF, 10 mM Na-pyrophosphate, 1 mM EGTA, 1.5 mM $MgCl_2$, 1 mM PMSF, 0.15 units/ml aprotinin and 20 µM leupeptin]. Lysates were cleared by centrifugation at 13,000 g for 10 min at 4° C. Immunoprecipitations were done as described in W. M. Kavanaugh, A. Klippel, J. A. Escobedo, L. T. Williams *Mol. Cell. Biol.* 12, 3415 (1992). SHC antibodies were raised against bacterially-expressed GST-SHC SH2 domain fusion protein essentially as described in Pelicci et al. *Cell* 70, 93–104 (1992).

Proteins having 52 kD, 66 kD and 145 kD were immunoprecipitated with anti-SHC. The 52 and 66-kD proteins correspond with the 52-kD SHC protein and 66-kD SHC related protein seen in fibroblasts (shown by the black arrows in FIG. 1; the pp145 proteins are indicated by the open arrows).

B. SHC Binding to pp145 Proteins

Proteins from PDGF stimulated cell lysates and from anti-SHC immunoprecipitates from quiescent (−) or PDGF-stimulated (+) Balb/c 3T3 cells were analyzed by SDS-PAGE and transferred to nitrocellulose. The filters were incubated with $^{32}$P-labeled GST-SHC fusion proteins as probes.

A full-length human cDNA clone of SHC was obtained from polymerase chain reaction (PCR) of K562 or SK cell cDNA on the basis of the published sequence. Sequencing revealed two differences from the published sequence: a silent T to C transition at position 1276, and an insertion of 3 bases (GCA) which resulted in an in-frame alanine insertion corresponding to amino acid 308. Because all clones contained the same changes, this likely represents a polymorphism. The cDNA was cloned into a baculovirus expression vector (pV-IKS) which contained, from 5' to 3': the glutathione S-transferase gene, the influenza virus hemagglutinin (IHA) epitope tag, a recognition sequence for cAMP-dependent protein kinase, and the SHC gene. Proteins were expressed by infecting Sf9 insect cells with recombinant baculovirus as described in D. K. Morrison et al. *Cell* 58, 649–657 (1989), M. D. Summers and G. E. Smith, *A Manual of Methods for Baculovirus Vectors and Insect Cell Culture Procedures*. (Texas Agricultural Station, College Station, Tex., 1987). Deletions of SHC indicated in FIG. 2C were obtained by PCR and cloned into the same vector. GST-SHC fusion proteins were purified by binding to glutathione-agarose (K. Guan and J. E. Dixon *Anal. Biochem.* 192, 262–267(1991)). The bound proteins were then incubated in 20 mM Tris-HCL (pH 7.5), 1 mM DTT, 100 mM NaCl, 12 mM $MgCl_2$, 0.5 mCi of gamma-$^{32}$P-ATP (6000 Ci/mmol), and 250 units of cAMP-dependent protein kinase catalytic subunit from bovine heart for 1 hour at room temperature. The agarose beads were then washed extensively and eluted with 10 mM glutathione. The specific activity of all preparations was typically $>1 \times 10^7$ cpm/µg. SDS-PAGE analysis demonstrated a single band at the predicted sizes for the GST-SHC fusion proteins by either Coomassie staining or autoradiography. Immunoprecipitates or portions of cell lysates containing equal amounts of total protein were separated by SDS-PAGE and transferred to nitrocellulose. The filters were blocked for 2 hours at 4° C. in nonfat dry milk (5%) in hybridization buffer [20 mM HEPES (pH 7.7), 75 mM KCl, 0.1 mM EDTA, 2.5 mM $MgCl_2$, 1 mM DTT, and 0.05% Triton X-100]. The filters were then incubated overnight at 4° C. in hybridization buffer containing milk (1%) and $2.5 \times 10^5$ cpm/ml of $^{32}$P-labeled GST-SHC fusion protein as a probe. The filters were then washed three times in hybridization buffer with milk (1%), dried, and exposed to X-ray film with an intensifying screen for 6 to 36 hours at −70° C.

Figure 2A:
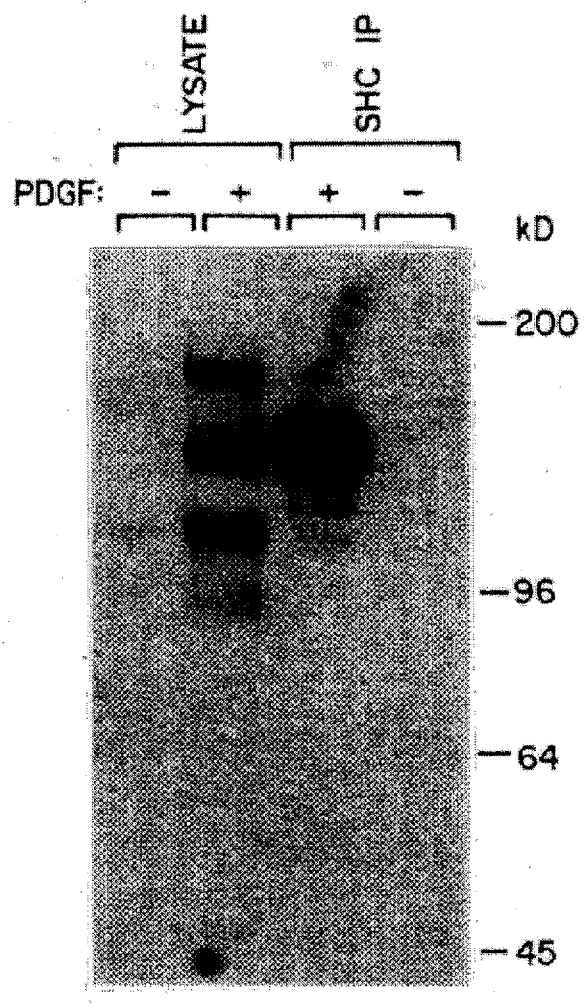
FIGS. 2A to 2D show binding of SHC to pp145. Panel A shows the binding of full-length SHC to proteins in cell lysates ("LYSATE") or in anti-SHC immunoprecipitates ("SHC IP") from quiescent (−) or PDGF-stimulated (+) Balb/c 3T3 cells. Panel B shows pp145 protein in lysates or anti-SHC immunoprecipitates from PDGF-stimulated fibroblasts, blotted with $^{32}$P-labeled SHC (left), SHC in which the SH2 domain had been deleted ("SHCΔSH2", residues 1 to 377, middle) or the isolated SHC SH2 domain ("SH2", residues 378 to 473, right). Panel C shows the deletional mapping of the pp145-binding domain on the SHC protein. Fragments of SHC corresponding to the indicated residues were prepared as $^{32}$P-labeled GST fusion proteins and as probes as described above. The organization of the SHC protein is shown, including the two translation start sites, the GRB2 binding site ("GRB2"), and the PTB domain (shown as the cross-hatched box), the collagen domain (shown as the vertically hatched box) and the SH2 domain (shown as the lightly shaded or white region). Also shown are blots of anti-SHC immunoprecipitates from PDGF-stimulated fibroblast lysates using three representative probes. Panel D shows the binding of the PTB domain. GST-SHCΔSH2 fusion protein containing an IHA epitope tag was incubated with lysate of activated B cells and then purified by immunoaffinity chromatography with monoclonal antibody to IHA ("PTB-IHA+lysate"), binding is shown by the absence of pp145 in the flowthrough, and its presence in the eluate. The controls ("Lysate alone" and "PTB-IHA alone") show no binding. The starting material ("Start"), column flow-through ("Flowthrough") and SDS eluates ("Eluate") were analyzed by blotting with $^{32}$P-labeled PTB domain probe as described above. The arrows within the lanes indicate the correct line-up of the labels for the lanes.
Figure 2B:
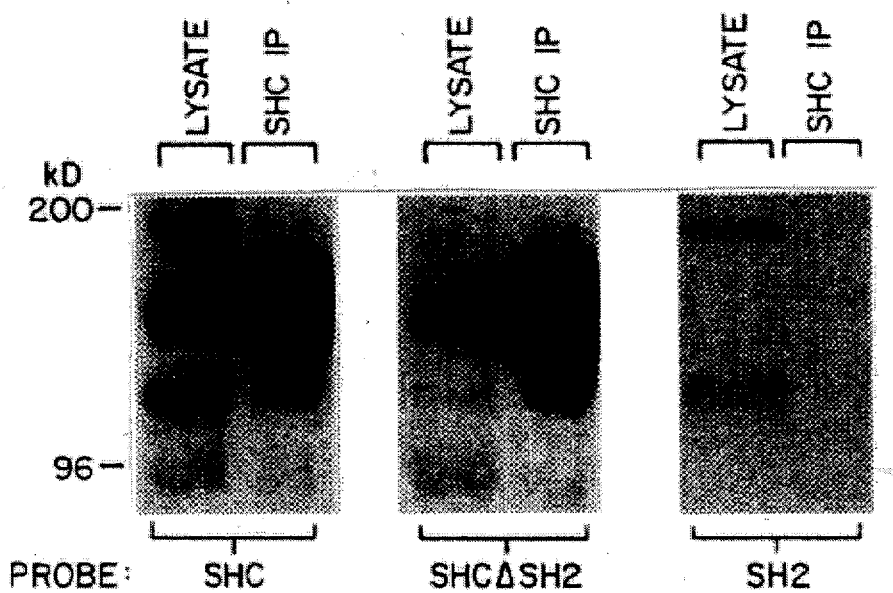
Figure 2C:
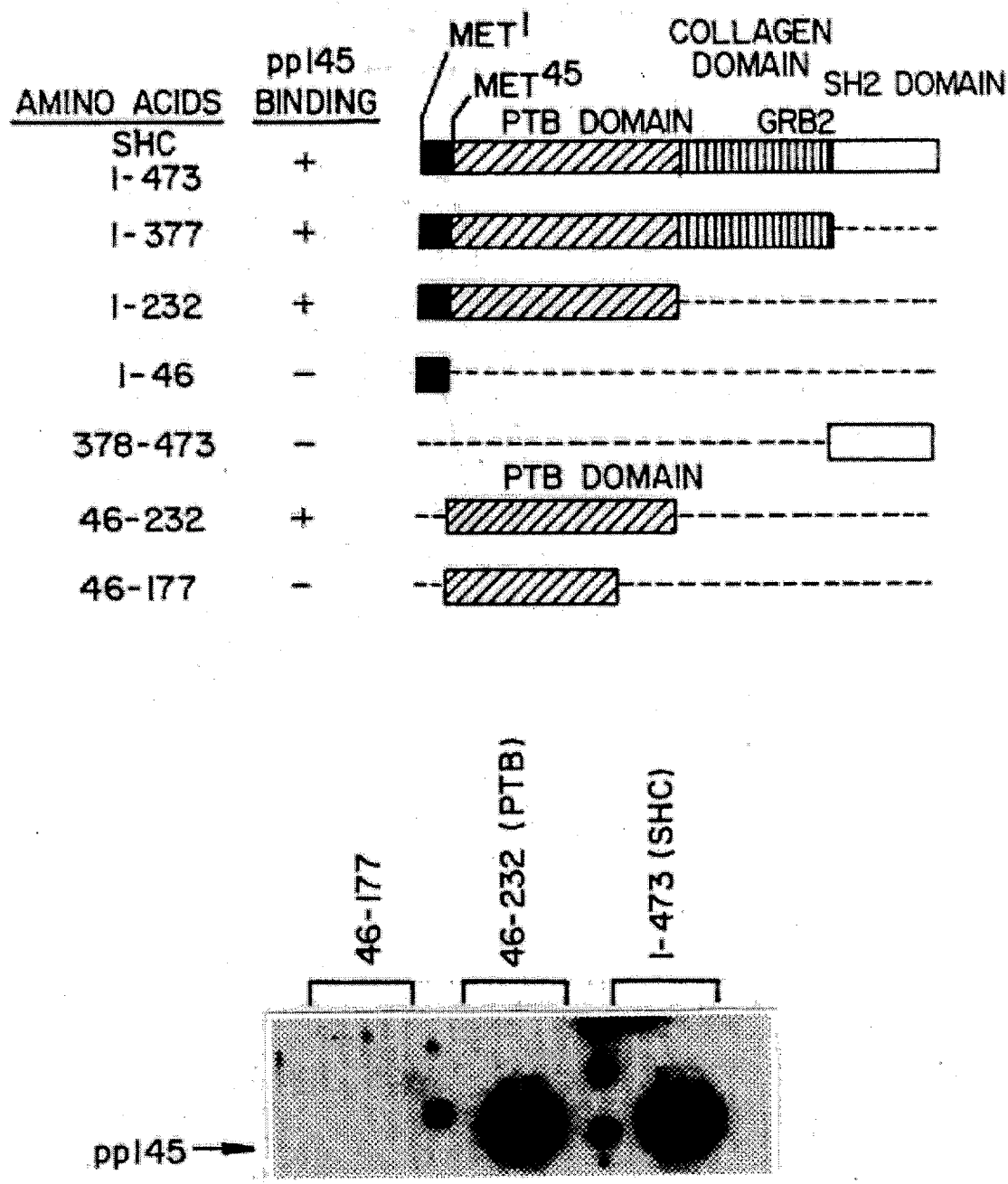
Figure 2D:
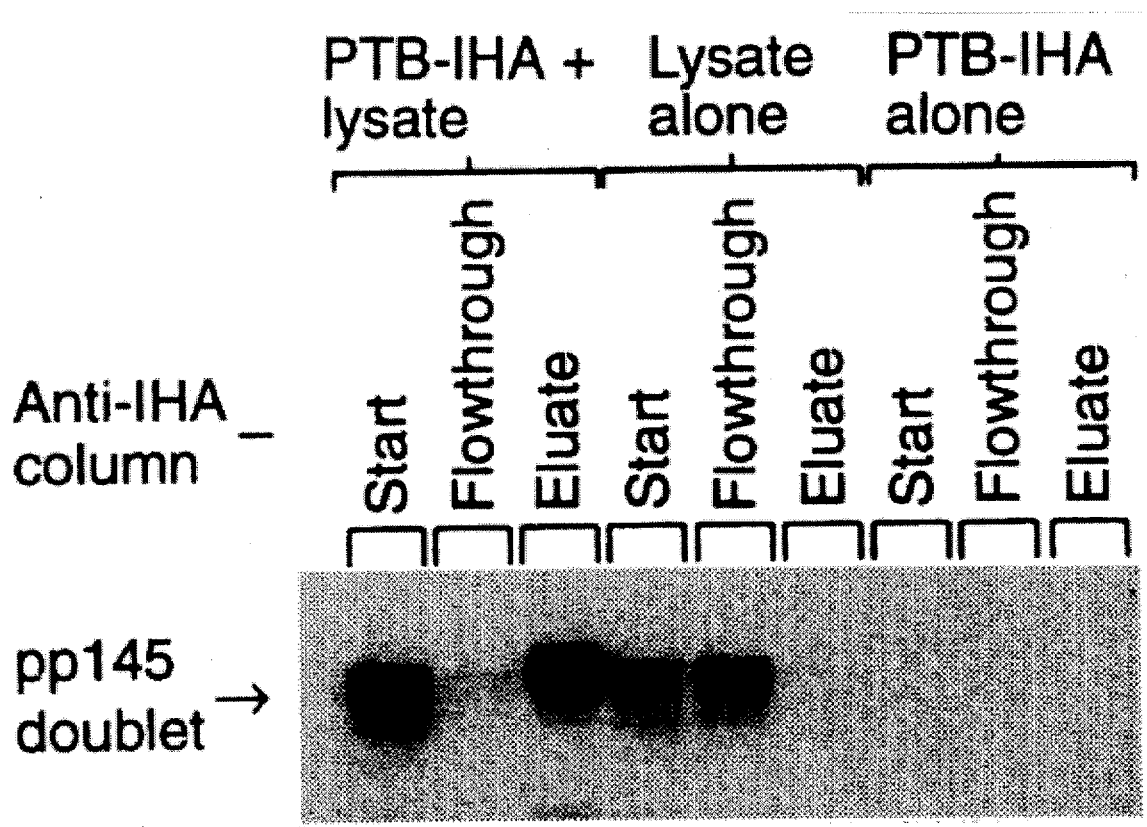

The results of blotting pp145 protein from lysates or anti-SHC immunoprecipitates from PDGF-stimulated fibroblasts blotted, with $^{32}$P-labeled SHC, SHC in which the SH2 domain had been deleted (SHCΔSH2, residues 1 to 377), and isolated SHC SH2 domain (residues 378 to 473), are shown as the left, middle and right panels of FIG. 2(B), respectively.

Deletion of the SHC SH2 domain eliminated binding to the 180 and 120 kD proteins from cell lysates but did not affect binding of SHC to the 145 kD proteins. The isolated SHC SH2 region bound to both the 120 and 180 kD proteins but did not bind to the 145 kD proteins. Further deletional analysis led to the 186 amino acid fragment of SHC (residues 46–232, the PTB domain) which bound the 145 kD protein without binding the 120 or 180 kD proteins.

The binding of the PTB domain to the 145 kD protein in solution was further investigated. GST-SHCΔSH2 protein containing the influenza virus hemagglutinin (IHA) epitope was incubated with lysate of activated B cells and then purified by immunoaffinity chromatography using monoclonal antibody to IHA.

Lysates were prepared in hybridization buffer from $2.5 \times 10^7$ Bal 17 cells stimulated by cross-linking the B cell antigen receptor as described in T. M. Saxton et al., *J. Immunol.* 153, 623–36 (1994). The lysate was incubated with approximately 250 ng of GST-SHCΔSH2 protein containing the IHA epitope tag for 1 hour at 4° C. The mixture was then subjected to immunoaffinity chromatography using a monoclonal antibody to IHA covalently attached or linked to agarose beads. The column was washed with 50 column volumes of hybridization buffer and eluted with 2% SDS. Proteins in equal fractions of the starting mixture, column flow-through and SDS eluate were separated by SDS-PAGE, transferred to nitrocellulose and blotted with $^{32}$P-labeled PTB domain protein probe. In B cells, pp145 is seen as a doublet. The starting material, column flow-through and SDS eluates were analyzed by blotting with $^{32}$P-labeled PTB domain probe as described above.

C. Phosphotyrosine Involvement in SHC-pp145 Binding

Proteins in anti-SHC immunoprecipitates from PDGF-stimulated fibroblasts were immobilized on nitrocellulose and treated with tyrosine-specific phosphatases ("PTPase") in the presence or absence of the PTPase inhibitor sodium orthovanadate.

Anti-SHC immunoprecipitates from PDGF-stimulated fibroblasts immobilized on nitrocellulose filters were incubated in 25 mM imidazole, pH 7.0, 50 mM NaCl, 2.5 mM EDTA, 5 mM DTT, 100 µg/ml acetylated bovine serum albumin and 5 units each of LAR and T cell tyrosine-specific phosphatases for 60 min at 30° C. An equivalent sample was treated identically except that 5 mM sodium orthovanadate was included. The filters were then washed extensively and blotted with $^{32}$P-GST-SHC as above, except that the hybridization buffer included 1 mM vanadate. The filters were then blotted with $^{32}$P-labeled GST-SHC or immunoblotted with antibody to phosphotyrosine. The results are shown in FIG. 3(A), top and bottom, respectively.

Lysates from PDGF-stimulated cells were blotted with $^{32}$P-labeled GST-SHC in the presence of the concentrations of phosphotyrosine or phosphoserine indicated in FIG. 3.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

---

What is claimed is:

1. A method of determining whether a test compound is an agonist or antagonist of a growth factor activation signaling pathway in a cell, comprising:
contacting the cell with the test compound in the presence of a growth factor;
lysing the cell to produce a cell lysate; and
determining an amount of a phosphorylated ligand to a PTB domain present in said cell lysate, said determining step comprising the steps of contacting the cell lysate with an isolated polypeptide which comprises a PTB domain, and which isolated polypeptide does not contain an SH2 domain, and determining an amount of protein in the cell lysate that binds to said isolated polypeptide; and
comparing the amount of phosphorylated ligand to a PTB domain from said determining step to an amount of phosphorylated ligand to a PTB domain in a cell lysate prepared from a cell contacted with a growth factor in the absence of said test compound, an increase or decrease in the amount of said phosphorylated ligand in the presence of said test compound being indicative that the compound is an agonist or antagonist of the growth factor activation signaling pathway, respectively.

2. The method of claim 1, wherein in said contacting step, said growth factor is selected from the group consisting of PDGF, FGF, EGF, insulin and insulin-like growth factor.

3. A method of determining if a test compound is an agonist or antagonist of PTB domain/phosphorylated ligand mediated regulatory system, the method comprising:
incubating the test compound with a polypeptide that comprises a PTB domain and which polypeptide does not contain an SH2 domain, and a phosphorylated ligand which is capable of interacting with said PTB domain to form a PTB domain/phosphorylated ligand complex, under conditions which permit the formation of said complex;

determining an amount of PTB domain/phosphorylated ligand complex formed in the presence of said test compound, and comparing said amount to an amount of PTB domain/phosphorylated ligand complex formed in the absence of the test compound;

an increase or decrease in the amount of PTB domain/phosphorylated ligand complex formed in the presence of the test compound over the amount of PTB domain/phosphorylated ligand complex formed in the absence of the test compound being indicative that the test compound is an agonist or antagonist of the PTB domain/phosphorylated ligand mediated regulatory system, respectively.

4. The method of claim 3, wherein said polypeptide comprising a PTB domain is covalently coupled to a solid support, and said phosphorylated ligand which is capable of interacting with said PTB domain is covalently coupled to a detectable group.

5. The method of claim 4, wherein said detectable group is selected from the group consisting of a radiolabel, a fluorescent label, an antibody binding epitope and an assayable enzyme.

6. The method of claim 4, wherein said step of determining the amount of PTB domain/phosphorylated ligand complex formed in the presence and absence of said test compound comprises determining the amount of detectable group that is bound to said solid support.

7. The method of claim 3, wherein said polypeptide comprising a PTB domain is covalently coupled to a detectable group, and said phosphorylated ligand which is capable of interacting with said PTB domain is covalently coupled to a solid support.

8. The method of claim 7, wherein said detectable group is selected from the group consisting of a radiolabel, a fluorescent label, an antibody binding epitope and an assayable enzyme.

9. The method of claim 7, wherein said step of determining the amount of PTB domain/phosphorylated ligand complex formed in the presence and absence of said test compound comprises determining the amount of detectable group that is bound to said solid support.

10. The method of claim 3, wherein said PTB domain/phosphorylated ligand mediated regulatory system is a growth factor activation signaling pathway in a cell.

11. The method of claim 10, wherein said growth factor activation signaling pathway is selected from the group consisting of PDGF, FGF, Insulin and Insulin-like growth factor activation signaling pathways.

12. A method of determining whether a test compound is an agonist or antagonist of a growth factor activation signaling pathway in a cell, comprising:

contacting the cell with the test compound in the presence of a growth factor;

lysing the cell to produce a cell lysate;

determining an amount of a phosphorylated ligand to a PTB domain present in said cell lysate, wherein said determining step comprises the steps of:

contacting the cell lysate with an isolated polypeptide having an amino acid sequence of a SCK phosphotyrosine binding domain, as shown in FIG. 4 (SEQ ID NO:2), or a phosphotyrosine binding fragment thereof; and determining an amount of protein in the cell lysate that binds to said polypeptide; and comparing the amount of phosphorylated ligand to a PTB domain from said determining step to an amount of phosphorylated ligand to a PTB domain in a cell lysate prepared from a cell contacted with a growth factor in the absence of said test compound, an increase or decrease in the amount of said phosphorylated ligand in the presence of said test compound being indicative that the compound is an agonist or antagonist of the growth factor activation signaling pathway, respectively.

13. The method of claim 12, wherein said polypeptide is covalently coupled to a detectable group, said detectable group being selected from the group consisting of a radiolabel, a fluorescent label an antibody binding epitope and an assayable enzyme.

14. The method of claim 13, wherein said cell lysate is immobilized upon a solid support, and said determining step comprises assaying for the presence of said detectable group bound to said solid support.

15. The method of claim 14, wherein said solid support is nitrocellulose.

16. The method of claim 14, wherein said solid support is a microtiter plate.

17. The method of claim 12, wherein said polypeptide is immobilized upon a solid support, and said determining step comprises determining an amount of protein from said cell lysate that binds to said solid support.

18. The method of claim 12, wherein said solid support is nitrocellulose.

19. The method of claim 12, wherein said solid support is a microtiter plate.

20. A method of determining if a test compound is an agonist or antagonist of PTB domain/phosphorylated ligand mediated regulatory system, the method comprising:

incubating the test compound with a polypeptide that comprises a PTB domain and which polypeptide does not contain an SH2 domain, and a phosphorylated ligand which is capable of interacting with said PTB domain to form a PTB domain/phosphorylated ligand complex, under conditions which permit the formation of said complex, wherein said polypeptide comprising a PTB domain has an amino acid sequence of a SCK phosphotyrosine binding domain as shown in FIG. 4 (SEQ ID NO:2), or a phosphotyrosine binding fragment thereof; and determining an amount of PTB domain/phosphorylated ligand complex formed in the presence of said test compound, and comparing said amount to an amount of PTB domain/phosphorylated ligand complex formed in the absence of the test compound;

an increase or decrease in the amount of PTB domain/phosphorylated ligand complex formed in the presence of the test compound over the amount of PTB domain/phosphorylated ligand complex formed in the absence of the test compound being indicative that the test compound is an agonist or antagonist of the PTB domain/phosphorylated ligand mediated regulatory system, respectively.

21. The method of claim 20, wherein in said incubating step, said phosphorylated ligand which is capable of interacting with said PTB domain is pp145.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 428 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:1:

```
Pro Gly Ser Gly Asp Ala Ala Ala Ala Glu Trp Ile Arg Lys Gly
  1               5                  10                  15

Ser Phe Ile His Lys Pro Ala His Gly Trp Leu His Pro Asp Ala Arg
                 20                  25                  30

Val Leu Gly Pro Gly Val Ser Tyr Val Val Arg Tyr Met Gly Cys Ile
             35                  40                  45

Glu Val Leu Arg Ser Met Arg Ser Leu Asp Phe Asn Thr Arg Thr Gln
 50                  55                  60

Val Thr Arg Glu Ala Ile Asn Arg Ile His Glu Ala Val Pro Gly Val
 65                  70                  75                  80

Arg Gly Ser Trp Lys Lys Ala Pro Asn Lys Ala Leu Ala Ser Val
                 85                  90                  95

Leu Gly Lys Ser Asn Leu Arg Phe Ala Gly Met Ser Ile Ser Ile His
                100                 105                 110

Ile Ser Thr Asp Gly Leu Ser Leu Ser Val Pro Ala Thr Arg Gln Val
            115                 120                 125

Ile Ala Asn His His Met Pro Ser Ile Ser Phe Ala Ser Gly Gly Asp
    130                 135                 140

Thr Asp Met Thr Asp Tyr Val Ala Tyr Val Ala Lys Asp Pro Ile Asn
145                 150                 155                 160

Gln Arg Ala Cys His Ile Leu Glu Cys Cys Glu Gly Leu Ala Gln Ser
                165                 170                 175

Ile Ile Ser Thr Val Gly Gln Ala Phe Glu Leu Arg Phe Lys Gln Tyr
            180                 185                 190

Leu His Ser Pro Pro Lys Val Ala Leu Pro Pro Glu Arg Leu Ala Gly
    195                 200                 205

Pro Glu Glu Ser Ala Trp Gly Asp Glu Glu Asp Ser Leu Glu His Asn
210                 215                 220

Tyr Tyr Asn Ser Ile Pro Gly Lys Glu Pro Pro Leu Gly Gly Leu Val
225                 230                 235                 240

Asp Ser Arg Leu Ala Leu Thr Gln Pro Cys Ala Leu Thr Ala Leu Asp
                245                 250                 255

Gln Gly Pro Ser Pro Ser Leu Arg Asp Ala Cys Ser Leu Pro Trp Asp
            260                 265                 270

Val Gly Ser Thr Gly Thr Ala Pro Pro Gly Asp Gly Tyr Val Gln Ala
    275                 280                 285

Asp Ala Arg Gly Pro Pro Asp His Glu Glu His Leu Tyr Val Asn Thr
    290                 295                 300

Gln Gly Leu Asp Ala Pro Glu Pro Glu Asp Ser Pro Lys Lys Asp Leu
305                 310                 315                 320

Phe Asp Met Arg Pro Phe Glu Asp Ala Leu Lys Leu His Glu Cys Ser
                325                 330                 335

Val Ala Ala Gly Val Thr Ala Ala Pro Leu Pro Leu Glu Asp Gln Trp
            340                 345                 350

Pro Ser Pro Pro Thr Arg Arg Ala Pro Val Ala Pro Thr Glu Glu Gln
    355                 360                 365

Leu Arg Gln Glu Pro Trp Tyr His Gly Arg Met Ser Arg Arg Ala Ala
    370                 375                 380

Glu Arg Met Leu Arg Ala Asp Gly Asp Phe Leu Val Arg Asp Ser Val
```

```
        385                 390                      395                      400
Thr  Asn  Pro  Gly  Gln  Tyr  Val  Leu  Thr  Gly  Met  His  Ala  Gly  Gln  Pro
                    405                      410                      415

Lys  His  Leu  Leu  Leu  Val  Asp  Pro  Glu  Gly  Val  Val
               420                      425
```

( 2 ) INFORMATION FOR SEQ ID NO:2:

( i ) SEQUENCE CHARACTERISTICS:
    ( A ) LENGTH: 184 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Leu  Gly  Pro  Gly  Val  Ser  Tyr  Val  Val  Arg  Tyr  Met  Gly  Cys  Ile  Glu
1                   5                        10                       15

Val  Leu  Arg  Ser  Met  Arg  Ser  Leu  Asp  Phe  Asn  Thr  Arg  Thr  Gln  Val
               20                       25                       30

Thr  Arg  Glu  Ala  Ile  Asn  Arg  Ile  His  Glu  Ala  Val  Pro  Gly  Val  Arg
          35                       40                       45

Gly  Ser  Trp  Lys  Lys  Lys  Ala  Pro  Asn  Lys  Ala  Leu  Ala  Ser  Val  Leu
     50                       55                       60

Gly  Lys  Ser  Asn  Leu  Arg  Phe  Ala  Gly  Met  Ser  Ile  Ser  Ile  His  Ile
65                       70                       75                       80

Ser  Thr  Asp  Gly  Leu  Ser  Leu  Ser  Val  Pro  Ala  Thr  Arg  Gln  Val  Leu
                    85                       90                       95

Ala  Asn  His  His  Met  Pro  Ser  Ile  Ser  Phe  Ala  Ser  Gly  Gly  Asp  Thr
               100                      105                      110

Asp  Met  Thr  Asp  Tyr  Val  Ala  Tyr  Val  Ala  Lys  Asp  Pro  Ile  Asn  Gln
               115                      120                      125

Arg  Ala  Cys  His  Ile  Leu  Glu  Cys  Cys  Glu  Gly  Leu  Ala  Gln  Ser  Ile
     130                      135                      140

Ile  Ser  Thr  Val  Gly  Gln  Ala  Phe  Glu  Leu  Arg  Phe  Lys  Gln  Tyr  Leu
145                      150                      155                      160

His  Ser  Pro  Pro  Lys  Val  Ala  Leu  Pro  Pro  Glu  Arg  Leu  Ala  Gly  Pro
               165                      170                      175

Glu  Glu  Ser  Ala  Trp  Gly  Asp  Glu
               180
```

( 2 ) INFORMATION FOR SEQ ID NO:3:

( i ) SEQUENCE CHARACTERISTICS:
    ( A ) LENGTH: 423 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:3:

```
Arg  Thr  Arg  Val  Glu  Gly  Gly  Gln  Leu  Gly  Gly  Glu  Glu  Trp  Thr  Arg
1                   5                        10                       15

His  Gly  Ser  Phe  Val  Asn  Lys  Pro  Thr  Arg  Gly  Trp  Leu  His  Pro  Asn
               20                       25                       30

Asp  Lys  Val  Met  Gly  Pro  Gly  Val  Ser  Tyr  Leu  Val  Arg  Tyr  Met  Gly
          35                       40                       45

Cys  Val  Glu  Val  Leu  Gln  Ser  Met  Arg  Ala  Leu  Asp  Phe  Asn  Thr  Arg
```

```
              50                       55                        60
     Thr  Gln  Val  Thr  Arg  Glu  Ala  Ile  Ser  Leu  Val  Cys  Glu  Ala  Val  Pro
     65                       70                  75                            80

Gly  Ala  Lys  Gly  Ala  Thr  Arg  Arg  Arg  Lys  Pro  Cys  Ser  Arg  Pro  Leu
                        85                       90                  95

Ser  Ser  Ile  Leu  Gly  Arg  Ser  Asn  Leu  Lys  Phe  Ala  Gly  Met  Pro  Ile
                        100                      105                      110

Thr  Leu  Thr  Val  Ser  Thr  Ser  Ser  Leu  Asn  Leu  Met  Ala  Ala  Asp  Cys
                   115                      120                 125

Lys  Gln  Ile  Ile  Ala  Asn  His  His  Met  Gln  Ser  Ile  Ser  Phe  Ala  Ser
                   130                      135                 140

Gly  Gly  Asp  Pro  Asp  Thr  Ala  Glu  Tyr  Val  Ala  Tyr  Val  Ala  Lys  Asp
     145                           150                 155                      160

Pro  Val  Asn  Gln  Arg  Ala  Cys  His  Ile  Leu  Glu  Cys  Pro  Glu  Gly  Leu
                             165                      170                      175

Ala  Gln  Asp  Val  Ile  Ser  Thr  Ile  Gly  Gln  Ala  Phe  Glu  Leu  Arg  Phe
                        180                      185                      190

Lys  Gln  Tyr  Leu  Arg  Asn  Pro  Pro  Lys  Leu  Val  Thr  Pro  His  Asp  Arg
                   195                      200                      205

Met  Ala  Gly  Phe  Asp  Gly  Ser  Ala  Trp  Asp  Glu  Glu  Glu  Glu  Glu  Pro
           210                           215                 220

Pro  Asp  His  Gln  Tyr  Tyr  Asn  Asp  Phe  Pro  Gly  Lys  Glu  Pro  Pro  Leu
     225                           230                      235                 240

Gly  Gly  Val  Val  Asp  Met  Arg  Leu  Arg  Glu  Gly  Ala  Ala  Pro  Gly  Ala
                             245                      250                      255

Ala  Arg  Pro  Thr  Ala  Pro  Asn  Ala  Gln  Thr  Pro  Ser  His  Leu  Gly  Ala
                        260                      265                      270

Thr  Leu  Pro  Val  Gly  Gln  Pro  Val  Gly  Gly  Asp  Pro  Glu  Val  Arg  Lys
                   275                      280                      285

Gln  Met  Pro  Pro  Pro  Pro  Cys  Pro  Ala  Gly  Arg  Glu  Leu  Phe  Asp
           290                      295                      300

Asp  Pro  Ser  Tyr  Val  Asn  Val  Gln  Asn  Leu  Asp  Lys  Ala  Arg  Gln  Ala
     305                      310                      315                      320

Val  Gly  Gly  Ala  Gly  Pro  Pro  Asn  Pro  Ala  Ile  Asn  Gly  Ser  Ala  Pro
                             325                      330                 335

Arg  Asp  Leu  Phe  Asp  Met  Lys  Pro  Phe  Glu  Asp  Ala  Leu  Arg  Val  Pro
                        340                      345                 350

Pro  Pro  Pro  Gln  Ser  Val  Ser  Met  Ala  Glu  Gln  Leu  Arg  Gly  Glu  Pro
                   355                      360                 365

Trp  Phe  His  Gly  Lys  Leu  Ser  Arg  Arg  Glu  Ala  Glu  Ala  Leu  Leu  Gln
           370                      375                 380

Leu  Asn  Gly  Asp  Phe  Leu  Val  Arg  Glu  Ser  Thr  Thr  Thr  Pro  Gly  Gln
     385                      390                 395                           400

Tyr  Val  Leu  Thr  Gly  Leu  Gln  Ser  Gly  Gln  Pro  Lys  His  Leu  Leu  Leu
                        405                      410                      415

Val  Asp  Pro  Glu  Gly  Val  Val
                        420
```

( 2 ) INFORMATION FOR SEQ ID NO:4:

( i ) SEQUENCE CHARACTERISTICS:
    ( A ) LENGTH: 186 amino acids
    ( B ) TYPE: amino acid
    ( C ) STRANDEDNESS: single
    ( D ) TOPOLOGY: linear (ii) MOLECULE TYPE: protein (xi) SEQUENCE DESCRIPTION: SEQ ID NO:4:

```
Met Gly Pro Gly Val Ser Tyr Leu Val Arg Tyr Met Gly Cys Val Glu
 1               5                  10                  15

Val Leu Gln Ser Met Arg Ala Leu Asp Phe Asn Thr Arg Thr Gln Val
            20                  25                  30

Thr Arg Glu Ala Ile Ser Leu Val Cys Glu Ala Val Pro Gly Ala Lys
        35                  40                  45

Gly Ala Thr Arg Arg Arg Lys Pro Cys Ser Arg Pro Leu Ser Ser Ile
    50                  55                  60

Leu Gly Arg Ser Asn Leu Lys Phe Ala Gly Met Pro Ile Thr Leu Thr
65                  70                  75                  80

Val Ser Thr Ser Ser Leu Asn Leu Met Ala Ala Asp Cys Lys Gln Ile
                85                  90                  95

Ile Ala Asn His His Met Gln Ser Ile Ser Phe Ala Ser Gly Gly Asp
                100                 105                 110

Pro Asp Thr Ala Glu Tyr Val Ala Tyr Val Ala Lys Asp Pro Val Asn
            115                 120                 125

Gln Arg Ala Cys His Ile Leu Glu Cys Pro Glu Gly Leu Ala Gln Asp
        130                 135                 140

Val Ile Ser Thr Ile Gly Gln Ala Phe Glu Leu Arg Phe Lys Gln Tyr
145                 150                 155                 160

Leu Arg Asn Pro Pro Lys Leu Val Thr Pro His Asp Arg Met Ala Gly
                165                 170                 175

Phe Asp Gly Ser Ala Trp Asp Lys Glu Glu
                180                 185
```

(2) INFORMATION FOR SEQ ID NO:5:

(i) SEQUENCE CHARACTERISTICS:
        (A) LENGTH: 1410 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1407

(xi) SEQUENCE DESCRIPTION: SEQ ID NO:5:

```
CCG GGG TCC GGG GAC GCC GCC GCC GCC GCC GAG TGG ATC CGG AAG GGC      48
Pro Gly Ser Gly Asp Ala Ala Ala Ala Ala Glu Trp Ile Arg Lys Gly
 1               5                  10                  15

AGC TTC ATC CAC AAA CCC GCG CAC GGC TGG CTA CAC CCC GAC GCC AGG      96
Ser Phe Ile His Lys Pro Ala His Gly Trp Leu His Pro Asp Ala Arg
            20                  25                  30

GTC CTG GGG CCC GGG GTC TCC TAC GTC GTG CGG TAC ATG GGC TGC ATC     144
Val Leu Gly Pro Gly Val Ser Tyr Val Val Arg Tyr Met Gly Cys Ile
        35                  40                  45

GAG GTT CTC CGC TCT ATG CGC TCC CTG GAC TTT AAC ACG CGC ACG CAG     192
Glu Val Leu Arg Ser Met Arg Ser Leu Asp Phe Asn Thr Arg Thr Gln
    50                  55                  60

GTG ACC AGG GAA GCC ATC AAC CGG CTC CAT GAG GCC GTG CCT GGC GTC     240
Val Thr Arg Glu Ala Ile Asn Arg Leu His Glu Ala Val Pro Gly Val
65                  70                  75                  80

CGG GGA TCC TGG AAG AAA AAG GCC CCC AAC AAG GCC CTG GCG TCC GTC     288
Arg Gly Ser Trp Lys Lys Lys Ala Pro Asn Lys Ala Leu Ala Ser Val
                85                  90                  95
```

-continued

| | | | | | | | | | | | | | | | | |
|---|---|---|---|---|---|---|---|---|---|---|---|---|---|---|---|---|
| CTG | GGC | AAG | AGC | AAC | CTT | CGC | TTT | GCC | GGC | ATG | AGC | ATC | TCC | ATC | CAC | 336 |
| Leu | Gly | Lys | Ser | Asn | Leu | Arg | Phe | Ala | Gly | Met | Ser | Ile | Ser | Ile | His | |
| | | 100 | | | | | 105 | | | | | 110 | | | | |
| ATC | TCC | ACT | GAT | GGC | CTC | AGC | CTC | TCC | GTG | CCT | GCC | ACG | CGC | CAG | GTC | 384 |
| Ile | Ser | Thr | Asp | Gly | Leu | Ser | Leu | Ser | Val | Pro | Ala | Thr | Arg | Gln | Val | |
| | | 115 | | | | 120 | | | | | 125 | | | | | |
| ATC | GCC | AAC | CAC | CAC | ATG | CCG | TCC | ATC | TCC | TTC | GCG | TCA | GGC | GGA | GAC | 432 |
| Ile | Ala | Asn | His | His | Met | Pro | Ser | Ile | Ser | Phe | Ala | Ser | Gly | Gly | Asp | |
| | 130 | | | | | 135 | | | | 140 | | | | | | |
| ACG | GAC | ATG | ACG | GAT | TAC | GTG | GCC | TAC | GTC | GCC | AAG | GAC | CCC | ATC | AAC | 480 |
| Thr | Asp | Met | Thr | Asp | Tyr | Val | Ala | Tyr | Val | Ala | Lys | Asp | Pro | Ile | Asn | |
| 145 | | | | | 150 | | | | 155 | | | | | 160 | | |
| CAG | AGA | GCC | TGC | CAC | ATC | CTG | GAG | TGC | TGT | GAG | GGC | CTG | GCA | CAG | AGC | 528 |
| Gln | Arg | Ala | Cys | His | Ile | Leu | Glu | Cys | Cys | Glu | Gly | Leu | Ala | Gln | Ser | |
| | | | | 165 | | | | 170 | | | | | 175 | | | |
| ATC | ATC | AGC | ACC | GTG | GGC | CAA | GCT | TTC | GAG | CTG | CGC | TTC | AAG | CAG | TAC | 576 |
| Ile | Ile | Ser | Thr | Val | Gly | Gln | Ala | Phe | Glu | Leu | Arg | Phe | Lys | Gln | Tyr | |
| | | | 180 | | | | | 185 | | | | 190 | | | | |
| CTG | CAC | AGC | CCG | CCC | AAG | GTG | GCG | CTG | CCC | CCA | GAA | AGG | CTG | GCA | GGG | 624 |
| Leu | His | Ser | Pro | Pro | Lys | Val | Ala | Leu | Pro | Pro | Glu | Arg | Leu | Ala | Gly | |
| | | 195 | | | | | 200 | | | | | 205 | | | | |
| CCG | GAG | GAG | TCG | GCC | TGG | GGG | GAC | GAG | GAG | GAC | TCT | TTG | GAG | CAC | AAT | 672 |
| Pro | Glu | Glu | Ser | Ala | Trp | Gly | Asp | Glu | Glu | Asp | Ser | Leu | Glu | His | Asn | |
| | 210 | | | | | 215 | | | | 220 | | | | | | |
| TAC | TAC | AAC | AGC | ATC | CCG | GGG | AAG | GAG | CCG | CCG | CTG | GGC | GGG | CTA | GTG | 720 |
| Tyr | Tyr | Asn | Ser | Ile | Pro | Gly | Lys | Glu | Pro | Pro | Leu | Gly | Gly | Leu | Val | |
| 225 | | | | | 230 | | | | 235 | | | | | 240 | | |
| GAC | TCC | AGG | CTG | GCC | CTG | ACA | CAG | CCC | TGC | GCC | CTC | ACG | GCC | CTC | GAC | 768 |
| Asp | Ser | Arg | Leu | Ala | Leu | Thr | Gln | Pro | Cys | Ala | Leu | Thr | Ala | Leu | Asp | |
| | | | | 245 | | | | 250 | | | | | 255 | | | |
| CAG | GGC | CCA | TCT | CCT | TCT | CTA | AGA | GAT | GCC | TGC | AGC | CTG | CCA | TGG | GAC | 816 |
| Gln | Gly | Pro | Ser | Pro | Ser | Leu | Arg | Asp | Ala | Cys | Ser | Leu | Pro | Trp | Asp | |
| | | | 260 | | | | 265 | | | | | 270 | | | | |
| GTG | GGG | TCC | ACC | GGT | ACA | GCT | CCA | CCG | GGG | GAC | GGC | TAC | GTG | CAG | GCG | 864 |
| Val | Gly | Ser | Thr | Gly | Thr | Ala | Pro | Pro | Gly | Asp | Gly | Tyr | Val | Gln | Ala | |
| | | 275 | | | | | 280 | | | | | 285 | | | | |
| GAC | GCC | CGG | GGC | CCC | CCG | GAC | CAC | GAG | GAG | CAC | CTG | TAT | GTC | AAC | ACC | 912 |
| Asp | Ala | Arg | Gly | Pro | Pro | Asp | His | Glu | Glu | His | Leu | Tyr | Val | Asn | Thr | |
| | 290 | | | | | 295 | | | | | 300 | | | | | |
| CAG | GGT | CTG | GAC | GCC | CCC | GAG | CCG | GAG | GAC | AGC | CCC | AAA | AAG | GAT | CTG | 960 |
| Gln | Gly | Leu | Asp | Ala | Pro | Glu | Pro | Glu | Asp | Ser | Pro | Lys | Lys | Asp | Leu | |
| 305 | | | | | 310 | | | | 315 | | | | | 320 | | |
| TTT | GAC | ATG | CGA | CCC | TTT | GAG | GAT | GCC | CTG | AAG | TTG | CAT | GAG | TGC | TCA | 1008 |
| Phe | Asp | Met | Arg | Pro | Phe | Glu | Asp | Ala | Leu | Lys | Leu | His | Glu | Cys | Ser | |
| | | | | 325 | | | | 330 | | | | | 335 | | | |
| GTG | GCG | GCA | GGC | GTG | ACA | GCA | GCC | CCT | CTT | CCC | TTG | GAG | GAC | CAG | TGG | 1056 |
| Val | Ala | Ala | Gly | Val | Thr | Ala | Ala | Pro | Leu | Pro | Leu | Glu | Asp | Gln | Trp | |
| | | | 340 | | | | | 345 | | | | 350 | | | | |
| CCC | AGC | CCC | CCT | ACC | CGC | CGG | GCC | CCT | GTG | GCC | CCC | ACG | GAG | GAA | CAG | 1104 |
| Pro | Ser | Pro | Pro | Thr | Arg | Arg | Ala | Pro | Val | Ala | Pro | Thr | Glu | Glu | Gln | |
| | | 355 | | | | | 360 | | | | | 365 | | | | |
| CTG | CGT | CAG | GAG | CCC | TGG | TAC | CAC | GGC | CGG | ATG | AGC | CGC | GGG | GCG | GCA | 1152 |
| Leu | Arg | Gln | Glu | Pro | Trp | Tyr | His | Gly | Arg | Met | Ser | Arg | Gly | Ala | Ala | |
| | 370 | | | | | 375 | | | | | 380 | | | | | |
| GAG | AGG | ATG | CTT | CGA | GCT | GAC | GGG | GAC | TTC | CTT | GTG | CGA | GAC | AGC | GTC | 1200 |
| Glu | Arg | Met | Leu | Arg | Ala | Asp | Gly | Asp | Phe | Leu | Val | Arg | Asp | Ser | Val | |
| 385 | | | | | 390 | | | | 395 | | | | | 400 | | |
| ACC | AAC | CCC | GGG | CAG | TAT | GTC | CTC | ACC | GGC | ATG | CAC | GCC | GGG | CAG | CCC | 1248 |
| Thr | Asn | Pro | Gly | Gln | Tyr | Val | Leu | Thr | Gly | Met | His | Ala | Gly | Gln | Pro | |
| | | | | 405 | | | | 410 | | | | | 415 | | | |

| | | | | | | | | | | | | | | | | |
|---|---|---|---|---|---|---|---|---|---|---|---|---|---|---|---|---|
| AAG | CAC | CTG | CTG | CTC | GTG | GAC | CCC | GAG | GGC | GTG | GTA | CGG | ACG | AAG | GAC | 1296 |
| Lys | His | Leu | Leu | Leu | Val | Asp | Pro | Glu | Gly | Val | Val | Arg | Thr | Lys | Asp | |
| | | 420 | | | | | | 425 | | | | | 430 | | | |
| GTG | CTG | TTT | GAG | AGC | ATC | AGC | CAC | CTG | ATC | GAC | CAC | CAC | CTG | CAG | AAC | 1344 |
| Val | Leu | Phe | Glu | Ser | Ile | Ser | His | Leu | Ile | Asp | His | His | Leu | Gln | Asn | |
| | | 435 | | | | | 440 | | | | | 445 | | | | |
| GGG | CAG | CCC | ATC | GTG | GCC | GCC | GAG | AGT | GAG | CTG | CAC | CTG | CGT | GGC | GTG | 1392 |
| Gly | Gln | Pro | Ile | Val | Ala | Ala | Glu | Ser | Glu | Leu | His | Leu | Arg | Gly | Val | |
| | 450 | | | | | 455 | | | | | 460 | | | | | |
| GTC | TCA | CGG | GAG | CCC | TGA | | | | | | | | | | | 1410 |
| Val | Ser | Arg | Glu | Pro | | | | | | | | | | | | |
| 465 | | | | | | | | | | | | | | | | |

(2) INFORMATION FOR SEQ ID NO:6:

(i) SEQUENCE CHARACTERISTICS:
    (A) LENGTH: 469 amino acids
    (B) TYPE: amino acid
    (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Pro | Gly | Ser | Gly | Asp | Ala | Ala | Ala | Ala | Glu | Trp | Ile | Arg | Lys | Gly |
| 1 | | | | 5 | | | | | 10 | | | | 15 | |
| Ser | Phe | Ile | His | Lys | Pro | Ala | His | Gly | Trp | Leu | His | Pro | Asp | Ala | Arg |
| | | | 20 | | | | | 25 | | | | | 30 | | |
| Val | Leu | Gly | Pro | Gly | Val | Ser | Tyr | Val | Val | Arg | Tyr | Met | Gly | Cys | Ile |
| | | | 35 | | | | 40 | | | | | 45 | | | |
| Glu | Val | Leu | Arg | Ser | Met | Arg | Ser | Leu | Asp | Phe | Asn | Thr | Arg | Thr | Gln |
| | 50 | | | | | 55 | | | | | 60 | | | | |
| Val | Thr | Arg | Glu | Ala | Ile | Asn | Arg | Leu | His | Glu | Ala | Val | Pro | Gly | Val |
| 65 | | | | | 70 | | | | | 75 | | | | | 80 |
| Arg | Gly | Ser | Trp | Lys | Lys | Lys | Ala | Pro | Asn | Lys | Ala | Leu | Ala | Ser | Val |
| | | | | 85 | | | | | 90 | | | | | 95 | |
| Leu | Gly | Lys | Ser | Asn | Leu | Arg | Phe | Ala | Gly | Met | Ser | Ile | Ser | Ile | His |
| | | | | 100 | | | | | 105 | | | | | 110 | |
| Ile | Ser | Thr | Asp | Gly | Leu | Ser | Leu | Ser | Val | Pro | Ala | Thr | Arg | Gln | Val |
| | | | 115 | | | | 120 | | | | | 125 | | | |
| Ile | Ala | Asn | His | His | Met | Pro | Ser | Ile | Ser | Phe | Ala | Ser | Gly | Gly | Asp |
| | | 130 | | | | 135 | | | | | 140 | | | | |
| Thr | Asp | Met | Thr | Asp | Tyr | Val | Ala | Tyr | Val | Ala | Lys | Asp | Pro | Ile | Asn |
| 145 | | | | | 150 | | | | | 155 | | | | | 160 |
| Gln | Arg | Ala | Cys | His | Ile | Leu | Glu | Cys | Cys | Glu | Gly | Leu | Ala | Gln | Ser |
| | | | | 165 | | | | | 170 | | | | | 175 | |
| Ile | Ile | Ser | Thr | Val | Gly | Gln | Ala | Phe | Glu | Leu | Arg | Phe | Lys | Gln | Tyr |
| | | | 180 | | | | | 185 | | | | | 190 | | |
| Leu | His | Ser | Pro | Pro | Lys | Val | Ala | Leu | Pro | Pro | Glu | Arg | Leu | Ala | Gly |
| | | | 195 | | | | 200 | | | | | 205 | | | |
| Pro | Glu | Glu | Ser | Ala | Trp | Gly | Asp | Glu | Glu | Asp | Ser | Leu | Glu | His | Asn |
| | 210 | | | | | 215 | | | | | 220 | | | | |
| Tyr | Tyr | Asn | Ser | Ile | Pro | Gly | Lys | Glu | Pro | Pro | Leu | Gly | Gly | Leu | Val |
| 225 | | | | | 230 | | | | | 235 | | | | | 240 |
| Asp | Ser | Arg | Leu | Ala | Leu | Thr | Gln | Pro | Cys | Ala | Leu | Thr | Ala | Leu | Asp |
| | | | | 245 | | | | | 250 | | | | | 255 | |
| Gln | Gly | Pro | Ser | Pro | Ser | Leu | Arg | Asp | Ala | Cys | Ser | Leu | Pro | Trp | Asp |
| | | | 260 | | | | | 265 | | | | | 270 | | |

| | | | | | | | | | | | | | | |
|---|---|---|---|---|---|---|---|---|---|---|---|---|---|---|
| Val | Gly | Ser | Thr | Gly | Thr | Ala | Pro | Pro | Gly | Asp | Gly | Tyr | Val | Gln | Ala |
| | | 275 | | | | | 280 | | | | | 285 | | | |
| Asp | Ala | Arg | Gly | Pro | Pro | Asp | His | Glu | Glu | His | Leu | Tyr | Val | Asn | Thr |
| | 290 | | | | | 295 | | | | | 300 | | | | |
| Gln | Gly | Leu | Asp | Ala | Pro | Glu | Pro | Glu | Asp | Ser | Pro | Lys | Lys | Asp | Leu |
| 305 | | | | | 310 | | | | 315 | | | | | | 320 |
| Phe | Asp | Met | Arg | Pro | Phe | Glu | Asp | Ala | Leu | Lys | Leu | His | Glu | Cys | Ser |
| | | | | 325 | | | | | 330 | | | | | 335 | |
| Val | Ala | Ala | Gly | Val | Thr | Ala | Ala | Pro | Leu | Pro | Leu | Glu | Asp | Gln | Trp |
| | | | 340 | | | | | 345 | | | | | 350 | | |
| Pro | Ser | Pro | Pro | Thr | Arg | Arg | Ala | Pro | Val | Ala | Pro | Thr | Glu | Glu | Gln |
| | | 355 | | | | | 360 | | | | | 365 | | | |
| Leu | Arg | Gln | Glu | Pro | Trp | Tyr | His | Gly | Arg | Met | Ser | Arg | Arg | Ala | Ala |
| | 370 | | | | | 375 | | | | | 380 | | | | |
| Glu | Arg | Met | Leu | Arg | Ala | Asp | Gly | Asp | Phe | Leu | Val | Arg | Asp | Ser | Val |
| 385 | | | | | 390 | | | | 395 | | | | | | 400 |
| Thr | Asn | Pro | Gly | Gln | Tyr | Val | Leu | Thr | Gly | Met | His | Ala | Gly | Gln | Pro |
| | | | | 405 | | | | | 410 | | | | | 415 | |
| Lys | His | Leu | Leu | Leu | Val | Asp | Pro | Glu | Gly | Val | Val | Arg | Thr | Lys | Asp |
| | | | 420 | | | | | 425 | | | | | 430 | | |
| Val | Leu | Phe | Glu | Ser | Ile | Ser | His | Leu | Ile | Asp | His | His | Leu | Gln | Asn |
| | | 435 | | | | | 440 | | | | | 445 | | | |
| Gly | Gln | Pro | Ile | Val | Ala | Ala | Glu | Ser | Glu | Leu | His | Leu | Arg | Gly | Val |
| | 450 | | | | 455 | | | | | 460 | | | | | |
| Val | Ser | Arg | Glu | Pro | | | | | | | | | | | |
| 465 | | | | | | | | | | | | | | | |

( 2 ) INFORMATION FOR SEQ ID NO:7:

( i ) SEQUENCE CHARACTERISTICS:
        ( A ) LENGTH: 1425 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1422

( x i ) SEQUENCE DESCRIPTION: SEQ ID NO:7:

| | | | | | | | | | | | | | | | |
|---|---|---|---|---|---|---|---|---|---|---|---|---|---|---|---|
| ATG | AAC | AAG | CTG | AGT | GGA | GGC | GGC | GGG | CGC | AGG | ACT | CGG | GTG | GAA | GGG | 48 |
| Met | Asn | Lys | Leu | Ser | Gly | Gly | Gly | Gly | Arg | Arg | Thr | Arg | Val | Glu | Gly | |
| 1 | | | | 5 | | | | | 10 | | | | | 15 | | |
| GGC | CAG | CTT | GGG | GGC | GAG | GAG | TGG | ACC | CGC | CAC | GGG | AGC | TTT | GTC | AAT | 96 |
| Gly | Gln | Leu | Gly | Gly | Glu | Glu | Trp | Thr | Arg | His | Gly | Ser | Phe | Val | Asn | |
| | | | 20 | | | | | 25 | | | | | 30 | | | |
| AAG | CCC | ACG | CGG | GGC | TGG | CTG | CAT | CCC | AAC | GAC | AAA | GTC | ATG | GGA | CCC | 144 |
| Lys | Pro | Thr | Arg | Gly | Trp | Leu | His | Pro | Asn | Asp | Lys | Val | Met | Gly | Pro | |
| | | 35 | | | | | 40 | | | | | 45 | | | | |
| GGG | GTT | TCC | TAC | TTG | GTT | CGG | TAC | ATG | GGT | TGT | GTG | GAG | GTC | CTC | CAG | 192 |
| Gly | Val | Ser | Tyr | Leu | Val | Arg | Tyr | Met | Gly | Cys | Val | Glu | Val | Leu | Gln | |
| | 50 | | | | | 55 | | | | | 60 | | | | | |
| TCA | ATG | CGT | GCC | CTG | GAC | TTC | AAC | ACC | CGG | ACT | CAG | GTC | ACC | AGG | GAG | 240 |
| Ser | Met | Arg | Ala | Leu | Asp | Phe | Asn | Thr | Arg | Thr | Gln | Val | Thr | Arg | Glu | |
| 65 | | | | | 70 | | | | | 75 | | | | | 80 | |
| GCC | ATC | AGT | CTG | GTG | TGT | GAG | GCT | GTG | CCG | GGT | GCT | AAG | GGG | GCG | ACA | 288 |
| Ala | Ile | Ser | Leu | Val | Cys | Glu | Ala | Val | Pro | Gly | Ala | Lys | Gly | Ala | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| AGG | AGG | AGA | AAG | CCC | TGT | AGC | CGC | CCG | CTC | AGC | TCT | ATC | CTG | GGG | AGG | 336 |
| Arg | Arg | Arg | Lys | Pro | Cys | Ser | Arg | Pro | Leu | Ser | Ser | Ile | Leu | Gly | Arg | |
| | | | 100 | | | | | 105 | | | | | 110 | | | |
| AGT | AAC | CTG | AAA | TTT | GCT | GGA | ATG | CCA | ATC | ACT | CTC | ACC | GTC | TCC | ACC | 384 |
| Ser | Asn | Leu | Lys | Phe | Ala | Gly | Met | Pro | Ile | Thr | Leu | Thr | Val | Ser | Thr | |
| | | 115 | | | | | 120 | | | | | 125 | | | | |
| AGC | AGC | CTC | AAC | CTC | ATG | GCC | GCA | GAC | TGC | AAA | CAG | ATC | ATC | GCC | AAC | 432 |
| Ser | Ser | Leu | Asn | Leu | Met | Ala | Ala | Asp | Cys | Lys | Gln | Ile | Ile | Ala | Asn | |
| | 130 | | | | | 135 | | | | | 140 | | | | | |
| CAC | CAC | ATG | CAA | TCT | ATC | TCA | TTT | GCA | TCC | GGC | GGG | GAT | CCG | GAC | ACA | 480 |
| His | His | Met | Gln | Ser | Ile | Ser | Phe | Ala | Ser | Gly | Gly | Asp | Pro | Asp | Thr | |
| 145 | | | | | 150 | | | | | 155 | | | | | 160 | |
| GCC | GAG | TAT | GTC | GCC | TAT | GTT | GCC | AAA | GAC | CCT | GTG | AAT | CAG | AGA | GCC | 528 |
| Ala | Glu | Tyr | Val | Ala | Tyr | Val | Ala | Lys | Asp | Pro | Val | Asn | Gln | Arg | Ala | |
| | | | | 165 | | | | | 170 | | | | | 175 | | |
| TGC | CAC | ATT | CTG | GAG | TGT | CCC | GAA | GGG | CTT | GCC | CAG | GAT | GTC | ATC | AGC | 576 |
| Cys | His | Ile | Leu | Glu | Cys | Pro | Glu | Gly | Leu | Ala | Gln | Asp | Val | Ile | Ser | |
| | | | 180 | | | | | 185 | | | | | 190 | | | |
| ACC | ATT | GGC | CAG | GCC | TTC | GAG | TTG | CGC | TTC | AAA | CAA | TAC | CTC | AGG | AAC | 624 |
| Thr | Ile | Gly | Gln | Ala | Phe | Glu | Leu | Arg | Phe | Lys | Gln | Tyr | Leu | Arg | Asn | |
| | | 195 | | | | | 200 | | | | | 205 | | | | |
| CCA | CCC | AAA | CTG | GTC | ACC | CCT | CAT | GAC | AGG | ATG | GCT | GGC | TTT | GAT | GGC | 672 |
| Pro | Pro | Lys | Leu | Val | Thr | Pro | His | Asp | Arg | Met | Ala | Gly | Phe | Asp | Gly | |
| | 210 | | | | | 215 | | | | | 220 | | | | | |
| TCA | GCA | TGG | GAT | GAG | GAG | GAG | GAA | GAG | CCA | CCT | GAC | CAT | CAG | TAC | TAT | 720 |
| Ser | Ala | Trp | Asp | Glu | Glu | Glu | Glu | Glu | Pro | Pro | Asp | His | Gln | Tyr | Tyr | |
| 225 | | | | | 230 | | | | | 235 | | | | | 240 | |
| AAT | GAC | TTC | CCG | GGG | AAG | GAA | CCC | CCC | TTG | GGG | GGG | GTG | GTA | GAC | ATG | 768 |
| Asn | Asp | Phe | Pro | Gly | Lys | Glu | Pro | Pro | Leu | Gly | Gly | Val | Val | Asp | Met | |
| | | | | 245 | | | | | 250 | | | | | 255 | | |
| AGG | CTT | CGG | GAA | GGA | GCC | GCT | CCA | GGG | GCT | GCT | CGA | CCC | ACT | GCA | CCC | 816 |
| Arg | Leu | Arg | Glu | Gly | Ala | Ala | Pro | Gly | Ala | Ala | Arg | Pro | Thr | Ala | Pro | |
| | | | 260 | | | | | 265 | | | | | 270 | | | |
| AAT | GCC | CAG | ACC | CCC | AGC | CAC | TTG | GGA | GCT | ACA | TTG | CCT | GTA | GGA | CAG | 864 |
| Asn | Ala | Gln | Thr | Pro | Ser | His | Leu | Gly | Ala | Thr | Leu | Pro | Val | Gly | Gln | |
| | | 275 | | | | | 280 | | | | | 285 | | | | |
| CCT | GTT | GGG | GGA | GAT | CCA | GAA | GTC | CGC | AAA | CAG | ATG | CCA | CCT | CCA | CCA | 912 |
| Pro | Val | Gly | Gly | Asp | Pro | Glu | Val | Arg | Lys | Gln | Met | Pro | Pro | Pro | Pro | |
| | 290 | | | | | 295 | | | | | 300 | | | | | |
| CCC | TGT | CCA | GCA | GGC | AGA | GAG | CTT | TTT | GAT | GAT | CCC | TCC | TAT | GTC | AAC | 960 |
| Pro | Cys | Pro | Ala | Gly | Arg | Glu | Leu | Phe | Asp | Asp | Pro | Ser | Tyr | Val | Asn | |
| 305 | | | | | 310 | | | | | 315 | | | | | 320 | |
| GTC | CAG | AAC | CTA | GAC | AAG | GCC | CGG | CAA | GCA | GTG | GGT | GGT | GCT | GGG | CCC | 1008 |
| Val | Gln | Asn | Leu | Asp | Lys | Ala | Arg | Gln | Ala | Val | Gly | Gly | Ala | Gly | Pro | |
| | | | | 325 | | | | | 330 | | | | | 335 | | |
| CCC | AAT | CCT | GCT | ATC | AAT | GGC | AGT | GCA | CCC | CGG | GAC | CTG | TTT | GAC | ATG | 1056 |
| Pro | Asn | Pro | Ala | Ile | Asn | Gly | Ser | Ala | Pro | Arg | Asp | Leu | Phe | Asp | Met | |
| | | | 340 | | | | | 345 | | | | | 350 | | | |
| AAG | CCC | TTC | GAA | GAT | GCT | CTT | CGG | GTG | CCT | CCA | CCT | CCC | CAG | TCG | GTG | 1104 |
| Lys | Pro | Phe | Glu | Asp | Ala | Leu | Arg | Val | Pro | Pro | Pro | Pro | Gln | Ser | Val | |
| | | 355 | | | | | 360 | | | | | 365 | | | | |
| TCC | ATG | GCT | GAG | CAG | CTC | CGA | GGG | GAG | CCC | TGG | TTC | CAT | GGG | AAG | CTG | 1152 |
| Ser | Met | Ala | Glu | Gln | Leu | Arg | Gly | Glu | Pro | Trp | Phe | His | Gly | Lys | Leu | |
| | 370 | | | | | 375 | | | | | 380 | | | | | |
| AGC | CGG | CGG | GAG | GCT | GAG | GCA | CTG | CTG | CAG | CTC | AAT | GGG | GAC | TTC | CTG | 1200 |
| Ser | Arg | Arg | Glu | Ala | Glu | Ala | Leu | Leu | Gln | Leu | Asn | Gly | Asp | Phe | Leu | |
| 385 | | | | | 390 | | | | | 395 | | | | | 400 | |
| GTA | CGG | GAG | AGC | ACG | ACC | ACA | CCT | GGC | CAG | TAT | GTG | CTC | ACT | GGC | TTG | 1248 |
| Val | Arg | Glu | Ser | Thr | Thr | Thr | Pro | Gly | Gln | Tyr | Val | Leu | Thr | Gly | Leu | |
| | | | | 405 | | | | | 410 | | | | | 415 | | |

```
CAG  AGT  GGG  CAG  CCT  AAG  CAT  TTG  CTA  CTG  GTG  GAC  CCT  GAG  GGT  GTG      1296
Gln  Ser  Gly  Gln  Pro  Lys  His  Leu  Leu  Leu  Val  Asp  Pro  Glu  Gly  Val
               420                 425                      430

GTT  CGG  ACT  AAG  GAT  CAC  CGC  TTT  GAA  AGT  GTC  AGT  CAC  CTT  ATC  AGC      1344
Val  Arg  Thr  Lys  Asp  His  Arg  Phe  Glu  Ser  Val  Ser  His  Leu  Ile  Ser
               435                 440                      445

TAC  CAC  ATG  GAC  AAT  CAC  TTG  CCC  ATC  ATC  TCT  GCG  GGC  AGC  GAA  CTG      1392
Tyr  His  Met  Asp  Asn  His  Leu  Pro  Ile  Ile  Ser  Ala  Gly  Ser  Glu  Leu
          450                 455                      460

TGT  CTA  CAG  CAA  CCT  GTG  GAG  CGG  AAA  CTG  TGA                                1425
Cys  Leu  Gln  Gln  Pro  Val  Glu  Arg  Lys  Leu
465                      470
```

( 2 ) INFORMATION FOR SEQ ID NO:8:

( i ) SEQUENCE CHARACTERISTICS:
        ( A ) LENGTH: 474 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Asn  Lys  Leu  Ser  Gly  Gly  Gly  Gly  Arg  Arg  Thr  Arg  Val  Glu  Gly
1                   5                   10                      15

Gly  Gln  Leu  Gly  Gly  Glu  Glu  Trp  Thr  Arg  His  Gly  Ser  Phe  Val  Asn
          20                  25                      30

Lys  Pro  Thr  Arg  Gly  Trp  Leu  His  Pro  Asn  Asp  Lys  Val  Met  Gly  Pro
               35                  40                  45

Gly  Val  Ser  Tyr  Leu  Val  Arg  Tyr  Met  Gly  Cys  Val  Glu  Val  Leu  Gln
          50                  55                      60

Ser  Met  Arg  Ala  Leu  Asp  Phe  Asn  Thr  Arg  Thr  Gln  Val  Thr  Arg  Glu
65                       70                       75                       80

Ala  Ile  Ser  Leu  Val  Cys  Glu  Ala  Val  Pro  Gly  Ala  Lys  Gly  Ala  Thr
                    85                  90                      95

Arg  Arg  Arg  Lys  Pro  Cys  Ser  Arg  Pro  Leu  Ser  Ser  Ile  Leu  Gly  Arg
               100                 105                     110

Ser  Asn  Leu  Lys  Phe  Ala  Gly  Met  Pro  Ile  Thr  Leu  Thr  Val  Ser  Thr
          115                 120                     125

Ser  Ser  Leu  Asn  Leu  Met  Ala  Ala  Asp  Cys  Lys  Gln  Ile  Ile  Ala  Asn
     130                 135                     140

His  His  Met  Gln  Ser  Ile  Ser  Phe  Ala  Ser  Gly  Gly  Asp  Pro  Asp  Thr
145                      150                     155                      160

Ala  Glu  Tyr  Val  Ala  Tyr  Val  Ala  Lys  Asp  Pro  Val  Asn  Gln  Arg  Ala
               165                 170                     175

Cys  His  Ile  Leu  Glu  Cys  Pro  Glu  Gly  Leu  Ala  Gln  Asp  Val  Ile  Ser
          180                 185                     190

Thr  Ile  Gly  Gln  Ala  Phe  Glu  Leu  Arg  Phe  Lys  Gln  Tyr  Leu  Arg  Asn
          195                 200                     205

Pro  Pro  Lys  Leu  Val  Thr  Pro  His  Asp  Arg  Met  Ala  Gly  Phe  Asp  Gly
     210                 215                     220

Ser  Ala  Trp  Asp  Glu  Glu  Glu  Glu  Pro  Pro  Asp  His  Gln  Tyr  Tyr
225                      230                     235                      240

Asn  Asp  Phe  Pro  Gly  Lys  Glu  Pro  Pro  Leu  Gly  Gly  Val  Val  Asp  Met
               245                 250                     255

Arg  Leu  Arg  Glu  Gly  Ala  Ala  Pro  Gly  Ala  Ala  Arg  Pro  Thr  Ala  Pro
          260                 265                     270

Asn  Ala  Gln  Thr  Pro  Ser  His  Leu  Gly  Ala  Thr  Leu  Pro  Val  Gly  Gln
```

-continued

|  | 275 |  |  |  |  | 280 |  |  |  | 285 |  |  |  |
|---|---|---|---|---|---|---|---|---|---|---|---|---|---|
| Pro | Val<br>290 | Gly | Gly | Asp | Pro | Glu<br>295 | Val | Arg | Lys | Gln | Met<br>300 | Pro | Pro | Pro | Pro |
| Pro<br>305 | Cys | Pro | Ala | Gly | Arg<br>310 | Glu | Leu | Phe | Asp | Asp<br>315 | Pro | Ser | Tyr | Val | Asn<br>320 |
| Val | Gln | Asn | Leu | Asp<br>325 | Lys | Ala | Arg | Gln | Ala<br>330 | Val | Gly | Gly | Ala | Gly<br>335 | Pro |
| Pro | Asn | Pro | Ala<br>340 | Ile | Asn | Gly | Ser | Ala<br>345 | Pro | Arg | Asp | Leu | Phe<br>350 | Asp | Met |
| Lys | Pro | Phe<br>355 | Glu | Asp | Ala | Leu | Arg<br>360 | Val | Pro | Pro | Pro<br>365 | Gln | Ser | Val |
| Ser | Met<br>370 | Ala | Glu | Gln | Leu | Arg<br>375 | Gly | Glu | Pro | Trp | Phe<br>380 | His | Gly | Lys | Leu |
| Ser<br>385 | Arg | Arg | Glu | Ala | Glu<br>390 | Ala | Leu | Leu | Gln | Leu<br>395 | Asn | Gly | Asp | Phe | Leu<br>400 |
| Val | Arg | Glu | Ser | Thr<br>405 | Thr | Thr | Pro | Gly | Gln<br>410 | Tyr | Val | Leu | Thr | Gly<br>415 | Leu |
| Gln | Ser | Gly | Gln<br>420 | Pro | Lys | His | Leu | Leu<br>425 | Leu | Val | Asp | Pro | Glu<br>430 | Gly | Val |
| Val | Arg | Thr<br>435 | Lys | Asp | His | Arg | Phe<br>440 | Glu | Ser | Val | Ser | His<br>445 | Leu | Ile | Ser |
| Tyr | His<br>450 | Met | Asp | Asn | His | Leu<br>455 | Pro | Ile | Ile | Ser | Ala<br>460 | Gly | Ser | Glu | Leu |
| Cys<br>465 | Leu | Gln | Gln | Pro | Val<br>470 | Glu | Arg | Lys | Leu |

( 2 ) INFORMATION FOR SEQ ID NO:9:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(2)
( D ) OTHER INFORMATION: /note= "Xaa is Ser or Thr."

( x i ) SEQUENCE DESCRIPTION: SEQ ID NO:9:

Gly Xaa Phe Leu Val Arg Glu Ser
1           5